(12) United States Patent
Ashton et al.

(10) Patent No.: US 8,663,182 B2
(45) Date of Patent: Mar. 4, 2014

(54) DISPOSABLE ABSORBENT ARTICLE WITH ABSORBENT WAISTCAP OR WAISTBAND AND METHOD FOR MAKING THE SAME

(75) Inventors: Gregory Ashton, Cincinnati, OH (US); Masaharu Nishikawa, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 453 days.

(21) Appl. No.: 12/476,270

(22) Filed: Jun. 2, 2009

(65) Prior Publication Data
US 2010/0305533 A1    Dec. 2, 2010

(51) Int. Cl.
*A61F 13/15* (2006.01)
*A61F 13/20* (2006.01)

(52) U.S. Cl.
USPC ............... 604/385.12; 604/367; 604/385.01

(58) Field of Classification Search
USPC ............... 604/367, 378, 385.01, 385.12
See application file for complete search history.

(56) References Cited

U.S. PATENT DOCUMENTS

| | | | |
|---|---|---|---|
| 3,848,594 A | 11/1974 | Buell | |
| 3,860,003 A | 1/1975 | Buell | |
| 4,610,678 A | 9/1986 | Weisman et al. | |
| 4,642,110 A * | 2/1987 | Dudek | 604/385.21 |
| 4,662,875 A | 5/1987 | Hirotsu et al. | |
| 4,834,735 A | 5/1989 | Alemany et al. | |
| 4,846,815 A | 7/1989 | Scripps | |
| 4,869,724 A | 9/1989 | Scripps | |
| 4,888,231 A | 12/1989 | Angstadt | |
| 4,940,464 A | 7/1990 | VanGompel et al. | |
| 5,037,416 A | 8/1991 | Allen et al. | |
| 5,092,861 A | 3/1992 | Nomura et al. | |
| 5,137,537 A | 8/1992 | Herron et al. | |
| 5,151,092 A | 9/1992 | Buell et al. | |
| 5,242,436 A | 9/1993 | Weil et al. | |
| 5,246,433 A | 9/1993 | Hasse et al. | |
| 5,260,345 A | 11/1993 | DesMarais et al. | |
| 5,269,775 A | 12/1993 | Freeland et al. | |
| 5,387,207 A | 2/1995 | Dyer et al. | |

(Continued)

FOREIGN PATENT DOCUMENTS

| | | |
|---|---|---|
| EP | 0 149 880 A2 | 7/1985 |
| WO | WO 95/16746 A1 | 6/1995 |
| WO | WO 02/064877 A2 | 8/2002 |
| WO | WO 2006/062258 A2 | 6/2006 |

OTHER PUBLICATIONS

PCT International Search Report mailed Aug. 26, 2009 (14 pages).
PCT International Search Report mailed Nov. 8, 2005 (17 pages).

*Primary Examiner* — Michele M Kidwell
(74) *Attorney, Agent, or Firm* — Andrew J. Mueller; Laura L. Whitmer

(57) ABSTRACT

A disposable absorbent article comprising an absorbent core having a garment surface and an opposed body surface, which surfaces meet along at least one longitudinal edge and at least one end edge; a liquid permeable topsheet positioned adjacent the body surface of the absorbent core and having a pair of opposed longitudinal edges; a liquid impermeable backsheet positioned adjacent the garment surface of the absorbent core; and a waistcap/waistband disposed adjacent to at least one projection associated with the absorbent core, wherein the waistcap/waistband is capable of absorbing moisture and subsequently deforming to fill at least a portion of space between the article and a portion of the wearer's body.

12 Claims, 18 Drawing Sheets

(56) References Cited

U.S. PATENT DOCUMENTS

| | | | |
|---|---|---|---|
| 5,397,316 A | | 3/1995 | LaVon et al. |
| 5,514,104 A | * | 5/1996 | Cole et al. ............... 604/366 |
| 5,554,145 A | | 9/1996 | Roe et al. |
| 5,569,234 A | | 10/1996 | Buell et al. |
| 5,571,096 A | | 11/1996 | Dobrin et al. |
| 5,591,150 A | * | 1/1997 | Olsen et al. ............ 604/385.23 |
| 5,591,155 A | | 1/1997 | Nishikawa et al. |
| 5,599,135 A | | 2/1997 | Goldman et al. |
| 5,649,920 A | | 7/1997 | Lavon et al. |
| 5,650,222 A | | 7/1997 | DesMarais et al. |
| 5,836,929 A | | 11/1998 | Bewick-Sonntag et al. |
| 5,836,930 A | | 11/1998 | Lantz et al. |
| 5,897,545 A | | 4/1999 | Kline et al. |
| 5,957,908 A | | 9/1999 | Kline et al. |
| 6,004,306 A | | 12/1999 | Robles et al. |
| 6,011,996 A | | 1/2000 | Gielen et al. |
| 6,120,487 A | | 9/2000 | Ashton |
| 6,120,489 A | | 9/2000 | Johnson et al. |
| 6,645,569 B2 | | 11/2003 | Cramer et al. |
| 6,794,557 B1 | | 9/2004 | Klemp et al. |
| 6,863,933 B2 | | 3/2005 | Cramer et al. |
| 7,112,621 B2 | | 9/2006 | Rohrbaugh et al. |
| 7,993,314 B2 | * | 8/2011 | Asp et al. ............... 604/348 |
| 7,993,319 B2 | * | 8/2011 | Sperl ................... 604/385.22 |
| 2003/0105190 A1 | | 6/2003 | Diehl et al. |
| 2003/0148684 A1 | | 8/2003 | Cramer et al. |
| 2003/0233082 A1 | | 12/2003 | Kline et al. |
| 2004/0127871 A1 | * | 7/2004 | Odorzynski et al. ......... 604/378 |
| 2004/0158212 A1 | | 8/2004 | Ponomarenko et al. |
| 2004/0162536 A1 | | 8/2004 | Becker et al. |
| 2005/0008839 A1 | | 1/2005 | Cramer et al. |
| 2005/0013992 A1 | | 1/2005 | Azad et al. |
| 2005/0030280 A1 | | 2/2005 | Gehlot et al. |
| 2005/0101928 A1 | | 5/2005 | Beruda et al. |
| 2005/0159720 A1 | | 7/2005 | Gentilcore et al. |
| 2005/0267428 A1 | * | 12/2005 | Ashton et al. ............... 604/368 |
| 2007/0118087 A1 | | 5/2007 | Flohr et al. |
| 2007/0156108 A1 | | 7/2007 | Becker et al. |

* cited by examiner

DISPOSABLE ABSORBENT ARTICLE WITH ABSORBENT WAISTCAP OR WAISTBAND AND METHOD FOR MAKING THE SAME

FIELD OF THE INVENTION

The invention generally relates to an absorbent article, and more particularly to a disposable absorbent garment, such as a taped diaper or training pant, with an absorbent waistcap or waistband.

BACKGROUND OF THE INVENTION

Absorbent articles, such as disposable diapers, training pants, and adult incontinence undergarments, absorb and contain body exudates. They also are intended to prevent body exudates from soiling, wetting, or otherwise contaminating clothing or other articles, such as bedding, that come in contact with the wearer. A disposable absorbent article, such as a disposable diaper, may be worn for several hours in a dry state or in a urine loaded state. Accordingly, efforts have been made toward improving the fit and comfort of the absorbent article to the wearer, both when the article is dry and when the article is fully or partially loaded with liquid exudate, while maintaining or enhancing the absorbing and containing functions of the article.

Contemporary absorbent articles often may include a topsheet, a backsheet, an absorbent core, a barrier cuff, and a gasketing cuff. The gasketing cuff is intended to prevent wicking and overflow from the fluid laden article to clothing contacting the edges of the article, in that the gasketing cuff presents a fluid impermeable barrier between the edge of the article and the contacting clothing. In addition, it provides a gasketing action about the legs of the wearer. The barrier cuff is intended to inhibit loose fecal matter or gushes of urine or liquids from soiling the wearer's clothing. The barrier cuff desirably restrains the free flow of this material and provides a structure to hold such material within the article.

In addition, contemporary absorbent articles may also include a waistband, which is sometimes known as a waistcap. The waistband or waistcap is intended to generate adequate stress to maintain fit of the article around the circumference of a wearer's body, such as a wearer's waist. Various waistbands or waistcaps can include tapes, fasteners, elastic, or other devices and materials to maintain the fit of the article or otherwise provide adjustment of the fit.

One common mode of failure for such absorbent article products occurs when body exudates leak out of product through gaps between the article and the wearer's torso or legs when the liquid exudate is not immediately absorbed within the article. Such leakage problems may be more likely to occur when the wearer is prone on his back. The failure mode may become more prevalent when an absorbent article is made better fitting and with a less bulky absorbent core, where the absorbent core cannot absorb the liquid exudate as rapidly as released by the wearer into the article. Accordingly, it would be desirable to increase the liquid volume holding capacity of the absorbent article to retain the free liquid exudate before and during absorption by the absorbent core. In addition, it would be desirable to maintain or enhance the liquid volume holding capacity of a thin, flexible absorbent article with minimum bulk and/or a narrow crotch for improved comfort.

SUMMARY OF THE INVENTION

Embodiments of the invention can address one or more of the foregoing technical problems and can provide a disposable absorbent article which may comprise an absorbent core having a garment surface and an opposed body surface, which surfaces meet along at least one longitudinal edge and at least one end edge; a liquid permeable topsheet positioned adjacent the body surface of the absorbent core and having a pair of opposed longitudinal edges; a liquid impermeable backsheet positioned adjacent the garment surface of the absorbent core; and a waistcap/waistband disposed adjacent to at least one projection associated with the absorbent material, wherein the waistcap/waistband is capable of absorbing moisture and subsequently deforming to fill at least a portion of space between the article and a portion of the wearer's body.

According to another aspect of this invention, a method is provided for constructing a disposable absorbent article having a waistcap/waistband comprising an absorbent material. The method includes the elements of providing an absorbent material for use in a disposable absorbent article comprising an absorbent particulate polymer material deposited on a substrate to form an absorbent material having a longitudinal axis extending from a first end to a second end such that the absorbent particulate polymer material present in the absorbent material has a basis weight that varies across the absorbent material in a direction substantially perpendicular to the longitudinal axis or in a direction substantially parallel to the longitudinal axis; and mounting the absorbent material to at least one waistcap/waistband for a disposable absorbent article.

Other features and aspects of the invention may be apparent from reading the following detailed description, drawings, and claims.

DETAILED DESCRIPTION OF EMBODIMENTS OF THE INVENTION

Figure 1:
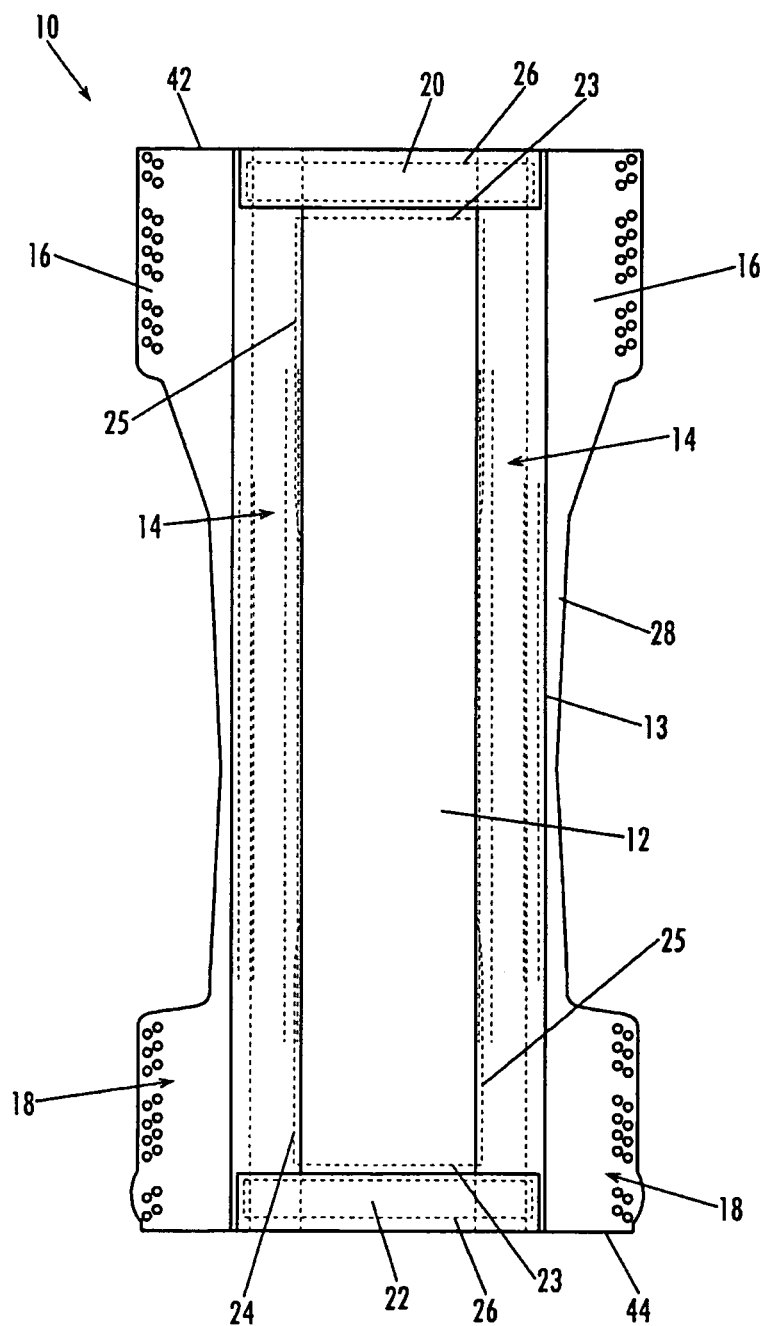
FIG. 1 is a plan view of an example diaper in accordance with an embodiment of the invention.

As summarized above, embodiments of the invention may encompass a disposable absorbent article, such as a diaper, and a method for constructing such a diaper having a waistcap/waistband comprising an absorbent material. Certain embodiments of the disposable article having a waistcap/waistband comprising an absorbent material can provide increased volume for retaining liquid exudate. By providing a disposable absorbent article with a waistcap/waistband including an absorbent material, such embodiments can enhance leakage prevention, particularly overnight leakage and leakage when the wearer is in the prone on back position. The use of an absorbent material that is substantially cellulose free may provide certain embodiments of the disposable absorbent article having a waistcap/waistband comprising an absorbent material with improved softness, flexibility, and conformity to a wearer's body for greater comfort without increasing the likelihood of leakage from the disposable absorbent article.

As used herein, the following terms have the following meanings:

"Absorbent article" refers to devices that absorb and contain body exudates, and, more specifically, refers to devices that are placed against or in proximity to the body of the wearer to absorb and contain the various exudates discharged from the body. Absorbent articles may include diapers, training pants, adult incontinence undergarments, feminine hygiene products, breast pads, care mats, bibs, wound dressing products, and the like. As used herein, the term "body fluids" or "body exudates" includes, but is not limited to, urine, blood, vaginal discharges, breast milk, sweat and fecal matter.

"Absorbent core" means a structure typically disposed between a topsheet and backsheet of an absorbent article for absorbing and containing liquid received by the absorbent article and may comprise one or more substrates, absorbent polymer material disposed on the one or more substrates, and a thermoplastic composition on the absorbent particulate polymer material and at least a portion of the one or more substrates for immobilizing the absorbent particulate polymer material on the one or more substrates. In a multilayer absorbent core, the absorbent core may also include a cover layer. The one or more substrates and the cover layer may comprise a nonwoven. Further, the absorbent core is substantially cellulose free. The absorbent core does not include an acquisition system, a topsheet, or a backsheet of the absorbent article. In a certain embodiment, the absorbent core would consist essentially of the one or more substrates, the absorbent polymer material, the thermoplastic composition, and optionally the cover layer.

"Absorbent material core" means a structure disposed within a waistcap/waistband. Construction of an absorbent material core using an absorbent polymer material is intended to be similar to that described for an absorbent core.

"Absorbent polymer material," "absorbent gelling material," "AGM," "superabsorbent," and "superabsorbent material" are used herein interchangeably and refer to cross linked polymeric materials that can absorb at least 5 times their weight of an aqueous 0.9% saline solution as measured using the Centrifuge Retention Capacity test (Edana 441.2-01).

"Absorbent particulate polymer material" is used herein to refer to an absorbent polymer material which is in particulate form so as to be flowable in the dry state.

"Absorbent particulate polymer material area" as used herein refers to the area of the core wherein the first substrate and second substrate are separated by a multiplicity of superabsorbent particles. The boundary of the absorbent particulate polymer material area is defined by the perimeter of the overlapping circles. There may be some extraneous superabsorbent particles outside of this perimeter between the first substrate and second substrate.

"Airfelt" is used herein to refer to comminuted wood pulp, which is a form of cellulosic fiber.

"Comprise," "comprising," and "comprises" are open ended terms, each specifies the presence of what follows, e.g., a component, but does not preclude the presence of other features, e.g., elements, steps, components known in the art, or disclosed herein.

"Consisting essentially of" is used herein to limit the scope of subject matter, such as that in a claim, to the specified materials or steps and those that do not materially affect the basic and novel characteristics of the subject matter.

"Disposable" is used in its ordinary sense to mean an article that is disposed or discarded after a limited number of usage events over varying lengths of time, for example, less than about 20 events, less than about 10 events, less than about 5 events, or less than about 2 events.

"Diaper" refers to an absorbent article generally worn by infants and incontinent persons about the lower torso so as to encircle the waist and legs of the wearer and that is specifically adapted to receive and contain urinary and fecal waste. As used herein, term "diaper" also includes "pants" which is defined below.

"Elastic", "elastically extensible", and "elasticized" refer herein to the property of a material and/or an element of a diaper or other disposable absorbent article whereby the material and/or the element can be elongated to at least 150% of its original unstretched length without rupture or catastrophic failure upon the application of tensioning force and will substantially return to its original length or near its original length after the tension is released.

"Fiber" and "filament" are used interchangeably.

A "nonwoven" is a manufactured sheet, web or batt of directionally or randomly orientated fibers, bonded by friction, and/or cohesion and/or adhesion, excluding paper and products which are woven, knitted, tufted, stitch-bonded incorporating binding yarns or filaments, or felted by wet-milling, whether or not additionally needled. The fibers may be of natural or man-made origin and may be staple or continuous filaments or be formed in situ. Commercially available fibers have diameters ranging from less than about 0.001 mm to more than about 0.2 mm and they come in several different forms: short fibers (known as staple, or chopped), continuous single fibers (filaments or monofilaments), untwisted bundles of continuous filaments (tow), and twisted bundles of continuous filaments (yarn). Nonwoven fabrics can be formed by many processes such as meltblowing, spunbonding, solvent spinning, electrospinning, and carding. The basis weight of nonwoven fabrics is usually expressed in grams per square meter (gsm).

"Pant" or "training pant", as used herein, refer to disposable garments having a waist opening and leg openings designed for infant or adult wearers. A pant may be placed in position on the wearer by inserting the wearer's legs into the leg openings and sliding the pant into position about a wearer's lower torso. A pant may be preformed by any suitable technique including, but not limited to, joining together portions of the article using refastenable and/or non-refastenable bonds (e.g., seam, weld, adhesive, cohesive bond, fastener, etc.). A pant may be preformed anywhere along the circumference of the article (e.g., side fastened, front waist fastened). While the terms "pant" or "pants" are used herein, pants are also commonly referred to as "closed diapers," "prefastened diapers," "pull-on diapers," "training pants," and "diaper-pants". Suitable pants are disclosed in U.S. Pat. No. 5,246,433, issued to Hasse, et al. on Sep. 21, 1993; U.S. Pat. No. 5,569,234, issued to Buell et al. on Oct. 29, 1996; U.S. Pat. No. 6,120,487, issued to Ashton on Sep. 19, 2000; U.S. Pat. No. 6,120,489, issued to Johnson et al. on Sep. 19, 2000; U.S. Pat. No. 4,940,464, issued to Van Gompel et al. on Jul. 10, 1990; U.S. Pat. No. 5,092,861, issued to Nomura et al. on Mar. 3, 1992; U.S. Patent Publication No. 2003/0233082 A1, entitled "Highly Flexible And Low Deformation Fastening Device", filed on Jun. 13, 2002; U.S. Pat. No. 5,897,545, issued to Kline et al. on Apr. 27, 1999; U.S. Pat. No. 5,957,908, issued to Kline et al on Sep. 28, 1999.

"Substantially cellulose free" is used herein to describe an article, such as an absorbent core, that contains less than 10% by weight cellulosic fibers, less than 5% cellulosic fibers, less than 1% cellulosic fibers, no cellulosic fibers, or no more than an immaterial amount of cellulosic fibers. An immaterial amount of cellulosic material would not materially affect the thinness, flexibility, or absorbency of an absorbent core.

"Substantially continuously distributed" as used herein indicates that within the absorbent particulate polymer material area, the first substrate and second substrate are separated by a multiplicity of superabsorbent particles. It is recognized that there may be minor incidental contact areas between the first substrate and second substrate within the absorbent particulate polymer material area. Incidental contact areas between the first substrate and second substrate may be intentional or unintentional (e.g. manufacturing artifacts) but do not form geometries such as pillows, pockets, tubes, quilted patterns and the like.

"Thermoplastic adhesive material" as used herein is understood to comprise a polymer composition from which fibers are formed and applied to the superabsorbent material with the intent to immobilize the superabsorbent material in both the dry and wet state. The thermoplastic adhesive material of the present invention forms a fibrous network over the superabsorbent material.

"Thickness" and "caliper" are used herein interchangeably.

"Waistcap/waistband", "waistcap", and "waistband" are used herein interchangeably and refer to a structure intended to provide circumferential pressure on a wearer's waist or adjacent part of the wearer's body. In some instances, a waistcap/waistband can be in multiple portions intended to be fastened together by any suitable fastening device or means.

FIG. 1 is a plan view of a diaper 10 according to a certain embodiment of the invention. The diaper 10 is shown in its flat out, uncontracted state (i.e., without elastic induced contraction). The diaper 10 is depicted in FIG. 1 with its longitudinal axis vertically oriented on the drawing, and its transverse axis horizontally oriented on the drawing. A portion of the diaper 10 that contacts a wearer is facing the viewer of FIG. 1. The diaper 10 may include a pair of elastically contractible cuffs 14 and an absorbent core 24 encased between a liquid permeable topsheet 12 and a liquid impermeable backsheet 28, the combination of the two sheets 12, 28 are generally referred to as the "chassis".

The absorbent core 24 may have a garment surface and an opposed body surface, which surfaces meet along one or more longitudinal edges 25 and one or more end edges 23. In certain embodiments, the portions of the absorbent core 24 comprising the one or more longitudinal edges 25 may be referred to as projections. The liquid permeable topsheet 12 may be positioned adjacent the body surface of the absorbent core 24 and may have a pair of opposed longitudinal edges 13. The liquid impermeable backsheet 28 may be positioned adjacent the garment surface of the absorbent core 24.

The diaper 10 may also include back side panel assemblies 16 and front side panel assemblies 18. The diaper 10 may also include a back waistcap/waistband 20 adjacent to a first end 42 and a front waistcap/waistband 22 adjacent to the opposite, second end 44. As shown in FIG. 1, the back waistcap/waistband 20 and the front waistcap/waistband 22 are respectively positioned to be immediately adjacent to the first end 42 and opposite, second end 44. The back waistcap/waistband 20 and the front waistcap/waistband 22 can also connect to the pair of elastically contractible cuffs 14 that extend across the length of the diaper 10. Each of the back waistcap/waistband 20 and the front waistcap/waistband 22 can include an absorbent material core 26 capable of absorbing moisture and subsequently deforming to fill at least a portion of space between the diaper 10 and a portion of a wearer's body. Construction techniques and materials for the absorbent material core 26 can be similar to those used for the absorbent core 24, and vice-versa, as described below. In certain embodiments, either or both the back waistcap/waistband 20 and the front waistcap/waistband 22 can include an absorbent material core 26. As shown in FIG. 1, the back waistcap/waistband 20 and the front waistcap/waistband 22 can span a portion of the width of the diaper 10. In other embodiments, the sizes of the back waistcap/waistband 20 and the front waistcap/waistband 22 can vary in width and/or height (shown as the vertical direction in FIG. 1), and may be oriented in other positions with respect to either or both the first end 42 and opposite, second end 44. In yet another example, a back waistcap/waistband and the front waistcap/waistband can span across the entire width of the diaper 10, and the height of each waistcap/waistband can overlap or otherwise be integrated with an intermediate portion of the diaper 10 as described below. Certain embodiments of the back waistcap/waistband and the front waistcap/waistband can be implemented in diapers with or without elastically contractible cuffs.

An intermediate portion of the diaper 10 may be configured as a crotch region, which extends longitudinally between the front and back waistcap/waistbands 20 and 22 shown in FIG. 1. In certain embodiments, the intermediate portion of the diaper 10 can be integrated with either or both front and back waistcap/waistbands 20 and 22. The waistcap/waistbands 20 and 22 may include elastic elements such that they gather about the waist of the wearer to provide improved fit and containment. The crotch region is that portion of the diaper 10 which, when the diaper 10 is worn, is generally positioned between the wearer's legs. The diaper 10 may also include such other features as are known in the art including front and rear ear panels, waist cap features, elastics and the like to provide better fit, containment and aesthetic characteristics. Such additional features are well known in the art and are e.g., described in U.S. Pat. No. 3,860,003 and U.S. Pat. No. 5,151,092.

The diaper 10 may also be provided with a closure system (also called a "fastening system") for fitting the diaper on the wearer. The closure system may take on a number of configurations such as adhesive tape tabs, mechanical closure tape tabs, fixed position fasteners, side seams as for training pants, or any other closure means as are known in the art. The closure system may include an adhesive tape tab fastening system including a pair of tape tab fastening members and a landing member, such as a reinforcing strip or, in the alternative, a portion of the backsheet, positioned in the front waist region of the diaper. Examples of suitable adhesive tape tab fastening systems are disclosed in U.S. Pat. No. 3,848,594 issued to Buell on Nov. 19, 1974; and U.S. Pat. No. 4,662,875 issued to Hirotsu and Robertson on May 5, 1987. Examples of other closure systems, including mechanical closure systems, useful in the present invention, are disclosed in U.S. Pat. No. 4,869,724 issued to Scripps on Sep. 26, 1989; U.S. Pat. No. 4,848,815 issued to Scripps on Jul. 11, 1989; and the two-point fastening system described in U.S. Pat. No. 5,242,436 issued to Weil, Buell, Clear, and Falcone on Sep. 7, 1993.

In at least one embodiment, in order to keep the diaper 10 in place about the wearer, at least a portion of the back waistcap/waistband 20 may be attached by at least one fastening member to at least a portion of the front waistcap/waistband 22 to form leg openings and an article waist. When fastened, the at least one fastening member can carry at least a portion of a tensile load around the article waist. In certain embodiments, an article user can hold at least one fastening member, and connect the back waistcap/waistband 20 to the front waistcap/waistband 22 in at least two places. This may be achieved through manipulation of bond strengths between multiple fastening members.

According to certain embodiments, the diaper 10 may be provided with a re-closable fastening system or may alternatively be provided in the form of a pant-type diaper. When the absorbent article is a diaper, it may comprise a re-closable fastening system joined to the chassis for securing the diaper to a wearer. When the absorbent article is a pant-type diaper, the article may comprise at least two side panels joined to the chassis and to each other to form a pant. The fastening system and any component thereof may include any material suitable for such a use, including but not limited to plastics, films, foams, nonwoven, woven, paper, laminates, fiber reinforced plastics and the like, or combinations thereof. In certain embodiments, the materials making up the fastening device may be flexible. The flexibility may allow the fastening system to conform to the shape of the body and thus, reduce the likelihood that the fastening system will irritate or injure the wearer's skin.

For unitary absorbent articles, the topsheet 12, the backsheet 28, and the absorbent core 24 may be assembled in a variety of well-known configurations, exemplary diaper configurations are described generally in U.S. Pat. No. 5,554,145 entitled "Absorbent Article With Multiple Zone Structural Elastic-Like Film Web Extensible Waist Feature" issued to Roe et al. on Sep. 10, 1996; U.S. Pat. No. 5,569,234 entitled "Disposable Pull-On Pant" issued to Buell et al. on Oct. 29, 1996; and U.S. Pat. No. 6,004,306 entitled "Absorbent Article With Multi-Directional Extensible Side Panels" issued to Robles et al. on Dec. 21, 1999.

The topsheet 12 in FIG. 1 may be fully or partially elasticized or may be foreshortened to provide a void space between the topsheet 12 and the absorbent core 24. Exemplary structures including elasticized or foreshortened topsheets are described in more detail in U.S. Pat. No. 5,037,416 entitled "Disposable Absorbent Article Having Elastically Extensible Topsheet" issued to Allen et al. on Aug. 6, 1991; and U.S. Pat. No. 5,269,775 entitled "Trisection Topsheets for Disposable Absorbent Articles and Disposable Absorbent Articles Having Such Trisection Topsheets" issued to Freeland et al. on Dec. 14, 1993.

The backsheet 28 may be joined with the topsheet 12. The backsheet 28 may prevent the exudates absorbed by the absorbent core 24 and contained within the diaper 10 from soiling other external articles that may contact the diaper 10, such as bed sheets and undergarments. In certain embodiments, the backsheet 28 may be substantially impervious to liquids (e.g., urine) and comprise a laminate of a nonwoven and a thin plastic film such as a thermoplastic film having a thickness of about 0.012 mm (0.5 mil) to about 0.051 mm (2.0 mils). Suitable backsheet films include those manufactured by Tredegar Industries Inc. of Terre Haute, Ind. and sold under the trade names X15306, X10962, and X10964. Other suitable backsheet materials may include breathable materials that permit vapors to escape from the diaper 10 while still preventing exudates from passing through the backsheet 28. Exemplary breathable materials may include materials such as woven webs, nonwoven webs, composite materials such as film-coated nonwoven webs, and microporous films such as manufactured by Mitsui Toatsu Co., of Japan under the designation ESPOIR NO and by EXXON Chemical Co., of Bay City, Tex., under the designation EXXAIRE. Suitable breathable composite materials comprising polymer blends are available from Clopay Corporation, Cincinnati, Ohio under the name HYTREL blend P18-3097. Such breathable composite materials are described in greater detail in PCT Application No. WO 95/16746, published on Jun. 22, 1995 in the name of E.I. DuPont. Other breathable backsheets including nonwoven webs and apertured formed films are described in U.S. Pat. No. 5,571,096 issued to Dobrin et al. on Nov. 5, 1996.

In certain embodiments, the backsheet of the present invention may have a water vapor transmission rate (WVTR) of greater than about 2000 g/24 h/m$^2$, greater than about 3000 g/24 h/m$^2$, greater than about 5000 g/24 h/m$^2$, greater than about 6000 g/24 h/m$^2$, greater than about 7000 g/24 h/m$^2$, greater than about 8000 g/24 h/m$^2$, greater than about 9000 g/24 h/m$^2$, greater than about 10000 g/24 h/m$^2$, greater than about 11000 g/24 h/m$^2$, greater than about 12000 g/24 h/m$^2$, greater than about 15000 g/24 h/m$^2$, measured according to WSP 70.5 (08) at 37.8° C. and 60% Relative Humidity.

Figure 2:
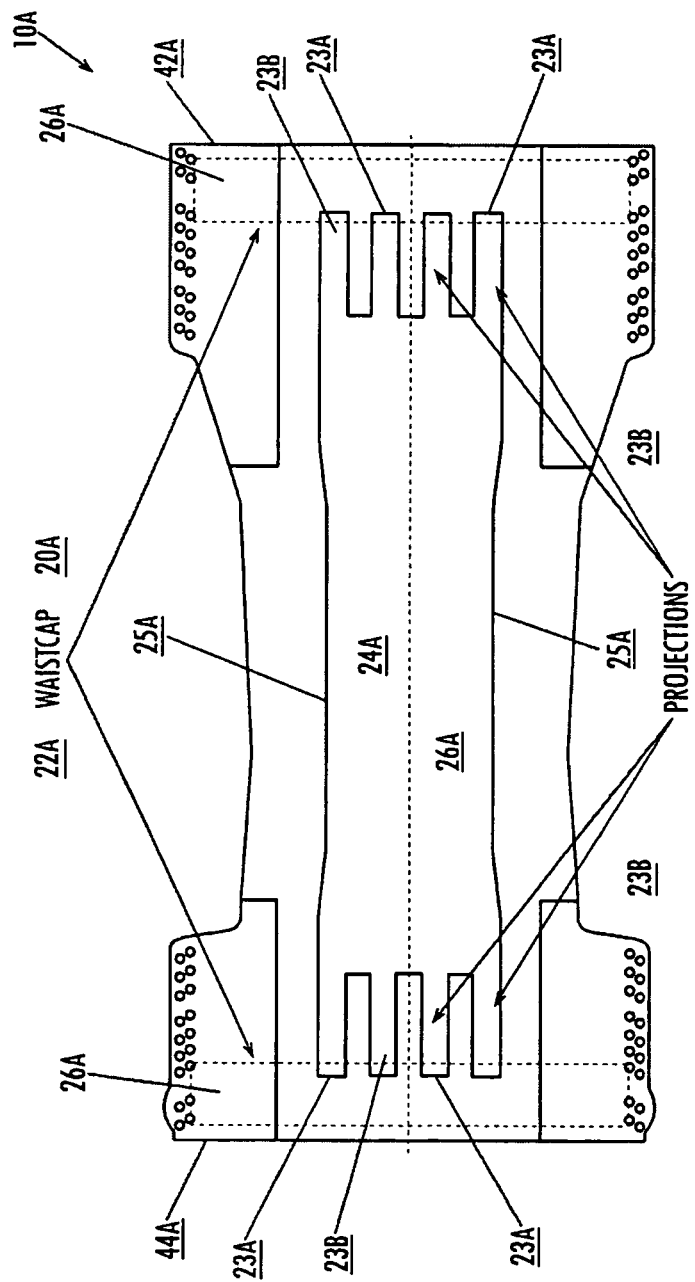
FIG. 2 is a plan view of another example diaper in accordance with an embodiment of the invention.

FIG. 2 is a plan view of a diaper 10A according to a certain embodiment of the invention. The diaper 10A is shown in its flat out, uncontracted state (i.e., without elastic induced contraction). The diaper 10A is depicted in FIG. 2 is similar to the diaper 10 shown in FIG. 1, and includes an absorbent core 24A with a different configuration than the absorbent core 24 in FIG. 1. The absorbent core 24A shown in FIG. 2 may have a garment surface and an opposed body surface, which surfaces meet along a series of end edges 23A and a series of longitudinal edges 25A. As shown in FIG. 2, the end edges 23A can be associated with a respective number of projections 23B of the absorbent core 24A. In certain embodiments, any number of projections 23B as well as respective end edges 23A can exist. Some or all of the projections 23B can extend adjacent to or otherwise be positioned slightly beneath a back waistcap/waistband 20A adjacent to a first end 42A and a front waistcap/waistband 22A adjacent to the opposite, second end 44A. As shown in FIG. 2 and similar to the orientations of the front waistcap/waistband 22 and back waistcap/waistband 20 to the ends 42, 44 in FIG. 1, the back waistcap/waistband 20A and the front waistcap/waistband 22A are respectively positioned to be immediately adjacent to the first end 42A and opposite, second end 44A. Similar to the diaper 10 in FIG. 1, the back waistcap/waistband 20A and the front waistcap/waistband 22A can also connect to the pair of elastically contractible cuffs that extend across the length of the diaper 10A.

The absorbent core 24A, back waistcap/waistband 20A, and front waistcap/waistband 22A shown in FIG. 2 can include an absorbent material core 26A, similar to 26 in FIG. 1, capable of absorbing moisture and subsequently deforming to fill at least a portion of space between the diaper 10A and a portion of a wearer's body. Construction techniques and materials for the absorbent material core 26A can be similar to those used for the absorbent core 24A, and vice-versa, as described with respect to the absorbent core 24 and absorbent core material 26A for the diaper 10 in FIG. 1.

Similar to the diaper 10 in FIG. 1, an intermediate portion of the diaper 10A may be configured as a crotch region, which extends longitudinally between the front and back waistcap/waistbands 20A and 22A shown in FIG. 2. In certain embodiments, the intermediate portion of the diaper 10A can be integrated with either or both front and back waistcap/waistbands 20A and 22A. The waistcap/waistbands 20A and 22A may include elastic elements such that they gather about the waist of the wearer to provide improved fit and containment. The crotch region is that portion of the diaper 10A which, when the diaper 10A is worn, is generally positioned between the wearer's legs. The diaper 10A may also include such other features as described with respect to the diaper 10 in FIG. 1 including a backsheet, topsheet, chassis, closure systems, fastening members, front and rear ear panels, waistcap features, elastics and the like to provide better fit, containment and aesthetic characteristics.

Figure 3:
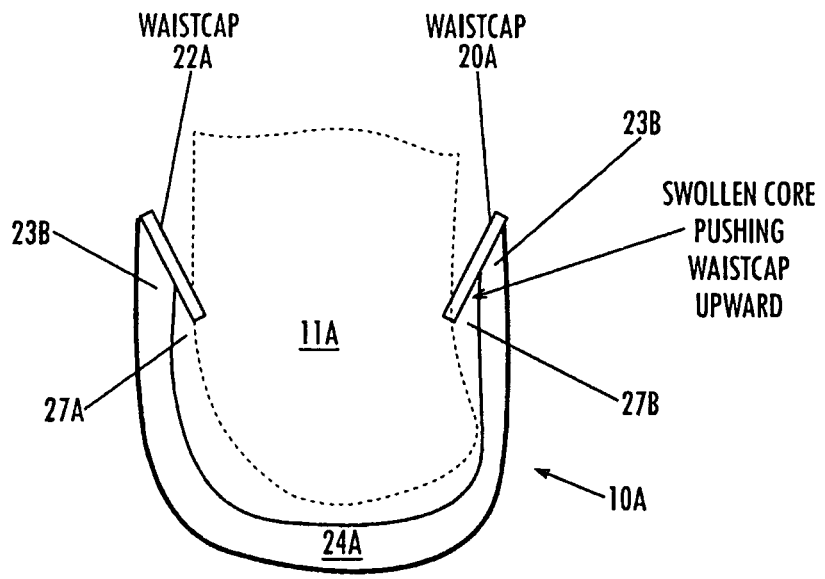
FIG. 3 is a side view of the example diaper shown in FIG. 2 wherein the diaper is shown on a wearer's body in accordance with an embodiment of the invention.

FIG. 3 is a side view of the example diaper 10A shown in FIG. 2 wherein the diaper 10A is shown on a wearer's body 11A in accordance with an embodiment of the invention. In the embodiment shown, when one or more projections 23B become wettened by fluid, respective portions of the absorbent core 24A may swell, and some or all of the wettened projections 23B can slightly elevate portions of the waistcap/waistbands 20A, 20B. In this manner, one or more channels 27A, 27B can form between the waistcaps/waistbands 20A, 20B and the projections 23B, and fluid can flow within the channels 27A, 27B and away from the wearer's body 11A. In a certain embodiment, greater elevation or lift of the waistcaps/waistbands 20A, 20B caused by increased swelling of some or all of the projections 23B can increase the possibility of fluid flow within channels 27A, 27B which may be formed between the waistcaps/waistbands 20A, 20B and the swollen projections 23B. When some or all of the fluid flows away from the wearer's body and within the channels 27A, 27B, the wearer can experience greater comfort since some or all of the fluid is kept away from the wearer's body 11A. Furthermore, decreased fluid intake and subsequent swelling by either or both of the waistcaps/waistbands 20A, 20B can help maintain contact pressure by the waistcaps/waistbands 20A, 20B about the circumference of the wearer's body 11A, thus maintaining sufficient contact pressure on the wearer's body. In certain instances, less skin marking and decreased likelihood of skin rashes on the wearer's body can result.

Figure 4:
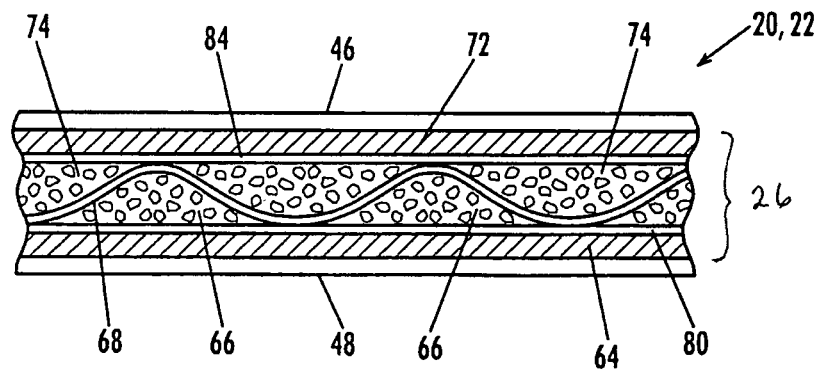
FIG. 4 is a cross-sectional view of an example waistcap/waistband in accordance with an embodiment of the invention.

The following description of diaper components is also intended to apply to the diaper embodiment 10A shown in FIGS. 2 and 3. FIG. 4 shows a cross-section of an example waistcap/waistband 20, 22 in accordance with an embodiment of the invention. As shown in FIG. 4, a waistcap/waistband such as 20 and 22 may be constructed of an absorbent material core 26 disposed between a waistcap/waistband top layer 46 and a waistcap/waistband back layer 48. Different layers or components of an absorbent material core may be used, such as one, two, three, four, five, six, or more, layers or components. As shown in FIG. 1, each waistcap/waistband 20, 22 may be secured to the topsheet 12 adjacent to the first end 42 or second, opposing end 44 of the topsheet 12.

Figure 11:
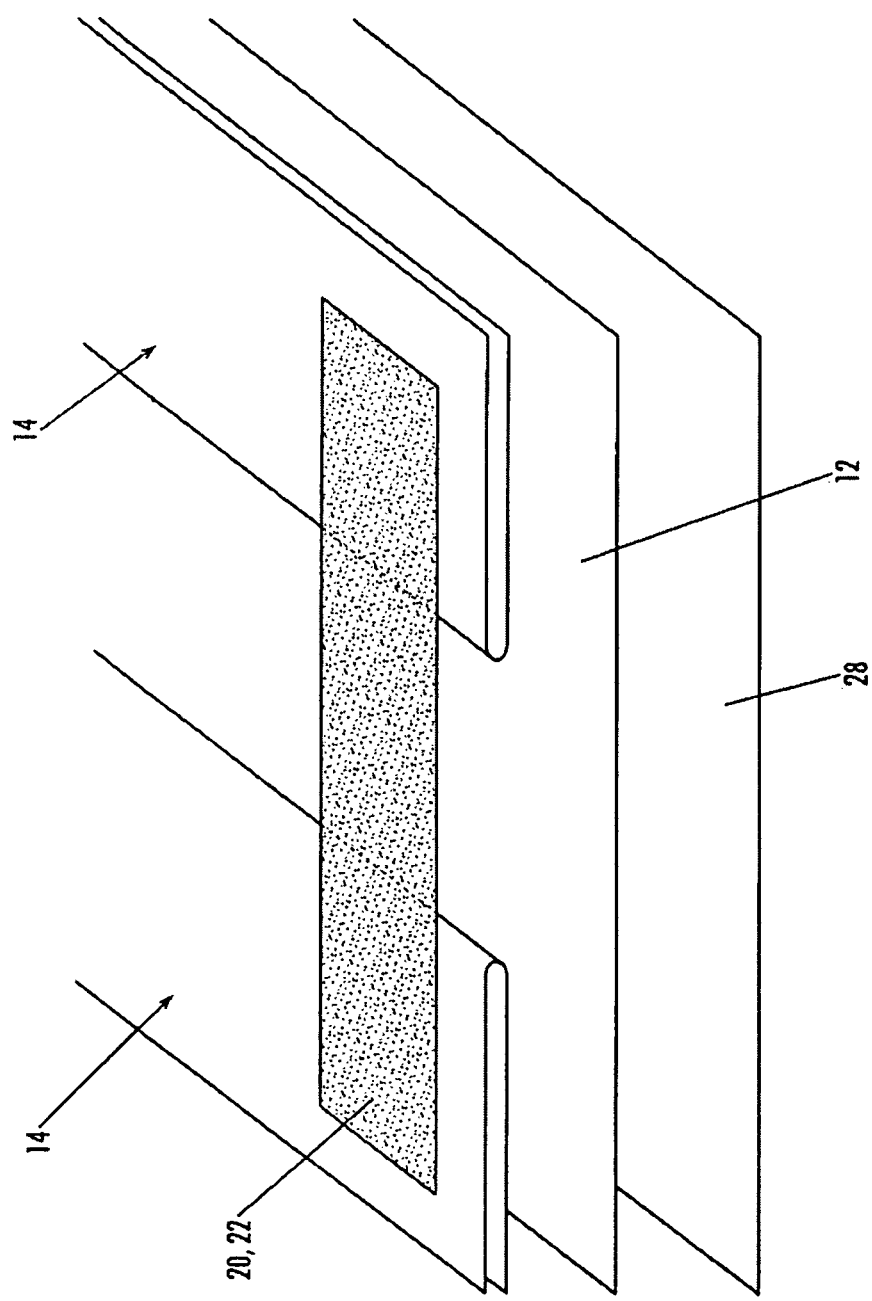
FIG. 11 is a schematic cross-sectional perspective view of an example waistcap/waistband and associated diaper in accordance with an embodiment of the invention.
Figure 12:
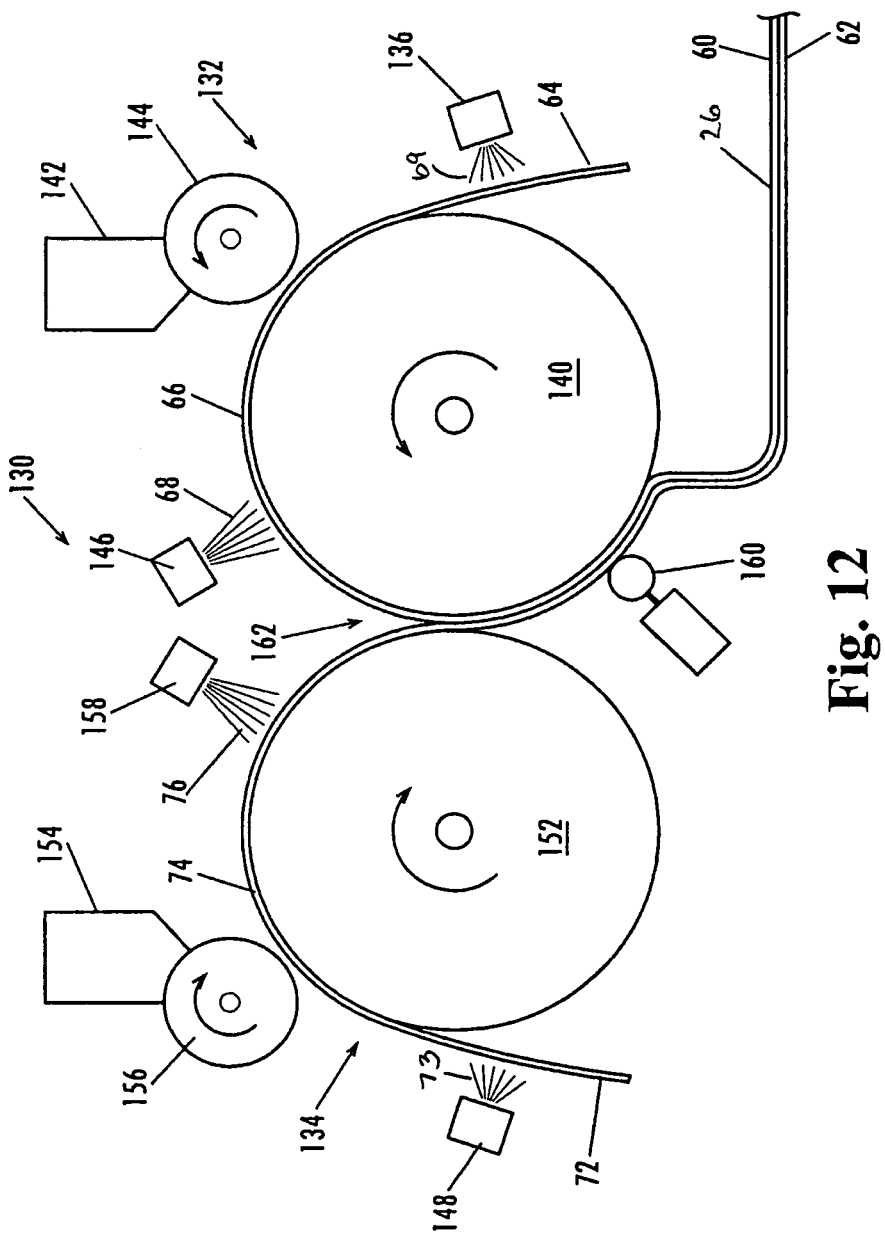
FIG. 12 is a schematic illustration of a process for making an example absorbent material core of a waistcap/waistband in accordance with an embodiment of the invention.

In certain embodiments, as shown in FIGS. 1 and 11, the elastically contractible cuffs 14 may be integrated with the waistcap/waistband 20, 22 to form a continuous gasket around the periphery of the absorbent area, i.e., around the absorbent core material 26 and absorbent core 24. The folding of the cuff material to form the cuff according to one embodiment of the invention creates pockets with waist features to form a 360 degree gasket. FIG. 12 also shows an example positioning and orientation of a waistcap/waistband 22 with respect to elastically contractible cuffs 14, a topsheet 12, and a backsheet 18 of a diaper 10. In certain embodiments without elastically contractible cuffs, a waistcap/waistband 20, 22 can be mounted to or otherwise integrated with the topsheet 12 of a diaper 10.

In a certain embodiment, the disposable absorbent article is a disposable training pant with the offset elastically contractible cuffs described herein and with elastically extensible side panels for improved fit and comfort. Examples of constructing the side panels and chassis are described in U.S. Pat. No. 5,246,433 to Hasse et al. and in U.S. Pat. No. 5,591,155 to Nishikawa et al.

As described above, embodiments of the diapers 10, 10A can include an absorbent material core 26, such as by printing or other placement of absorbent polymer onto the nonwoven material that forms a back waistcap/waistband 20 and/or front waistcap/waistband 22. In this manner, as each waistcap/waistband 20, 22 swells by way of absorbing moisture or fluid, and subsequently deforms to fill at least a portion of space between the diaper 10 and a portion of the wearer's body. Further, each waistcap/waistband 20, 22 may create regosity that allows moisture or fluid to be trapped under it, thereby preventing leakage, especially on subsequent loading of moisture or liquid exudate with slower acquisition. The waistcap/waistband 20, 22 also may help hold up the barrier leg cuff near the waist of the wearer. Because, the waistcap/ waistband 20, 22 can absorb at least a portion of moisture or fluid, an absorbent core associated with the article or diaper 10 can be designed with less absorbent material than in conventional articles or diapers, which can decrease the cost and may increase the flexibility of the crotch region of the diaper 10. Furthermore, due to the ability of certain embodiments of a waistcap/waistband 20, 22 to form a gasket, relatively less circumferential stress on the wearer's body may be generated, thereby reducing pressure marking on the wearer's body and lessening the possibility of skin irritation.

The absorbent particulate polymer material area, according to an exemplary embodiment, may have a relatively narrow width in the crotch area of the absorbent article for increased wearing comfort. Hence, the absorbent particulate polymer material area, according to an embodiment, may have a width as measured along a transverse line which is positioned at equal distance to the front edge and the rear edge of the absorbent article, which is less than about 100 mm, 90 mm, 80 mm, 70 mm, 60 mm or even less than about 50 mm.

It has been found that, for most absorbent articles such as diapers, the liquid discharge occurs predominately in the front half of the diaper. The front half of the absorbent core 14 should therefore comprise most of the absorbent capacity of the core. Thus, according to certain embodiments, the front half of the absorbent core may comprise more than about 60% of the superabsorbent material, or more than about 65%, 70%, 75%, 80%, 85%, or 90% of the superabsorbent material.

In certain embodiments, the absorbent material core 26 may further comprise any absorbent material that is generally compressible, conformable, non-irritating to the wearer's skin, and capable of absorbing and retaining liquids such as urine and other certain body exudates. In such embodiments, the absorbent material core 26 may comprise a wide variety of liquid-absorbent materials commonly used in disposable diapers and other absorbent articles such as comminuted wood pulp, which is generally referred to as airfelt, creped cellulose wadding, melt blown polymers, including co-form, chemically stiffened, modified or cross-linked cellulosic fibers, tissue, including tissue wraps and tissue laminates, absorbent foams, absorbent sponges, or any other known absorbent material or combinations of materials. The absorbent material core 26 may further comprise minor amounts (typically less than about 10%) of non-liquid absorbent materials, such as adhesives, waxes, oils and the like.

Exemplary absorbent structures for use as the absorbent assemblies are described in U.S. Pat. No. 4,610,678 (Weisman et al.); U.S. Pat. No. 4,834,735 (Alemany et al.); U.S. Pat. No. 4,888,231 (Angstadt); U.S. Pat. No. 5,260,345 (DesMarais et al.); U.S. Pat. No. 5,387,207 (Dyer et al.); U.S. Pat. No. 5,397,316 (LaVon et al.); and U.S. Pat. No. 5,625,222 (DesMarais et al.).

Figure 5:
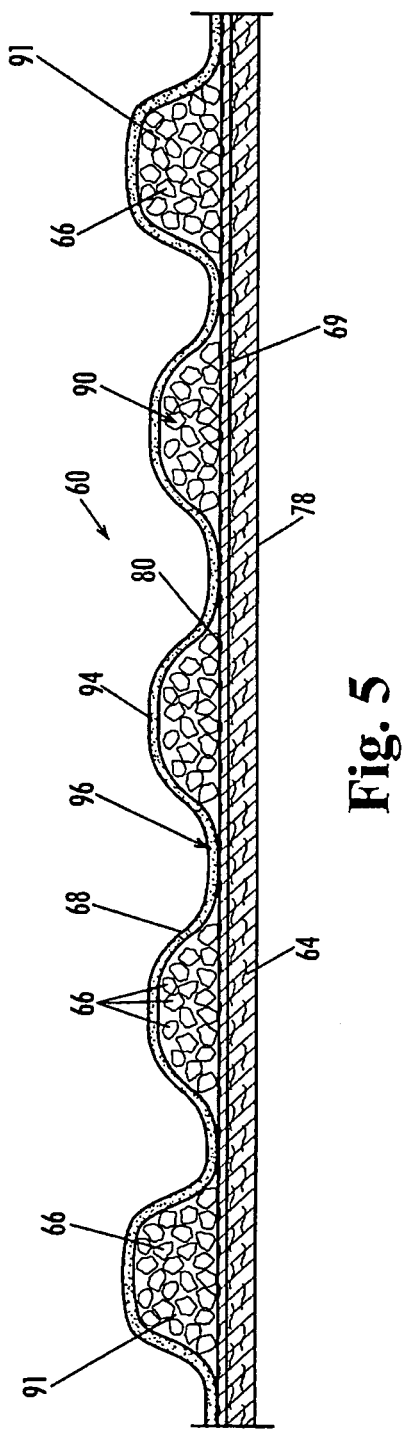
FIG. 5 is a partial cross-sectional view of an example absorbent material core layer for a waistcap/waistband in accordance with an embodiment of the invention.
Figure 6:
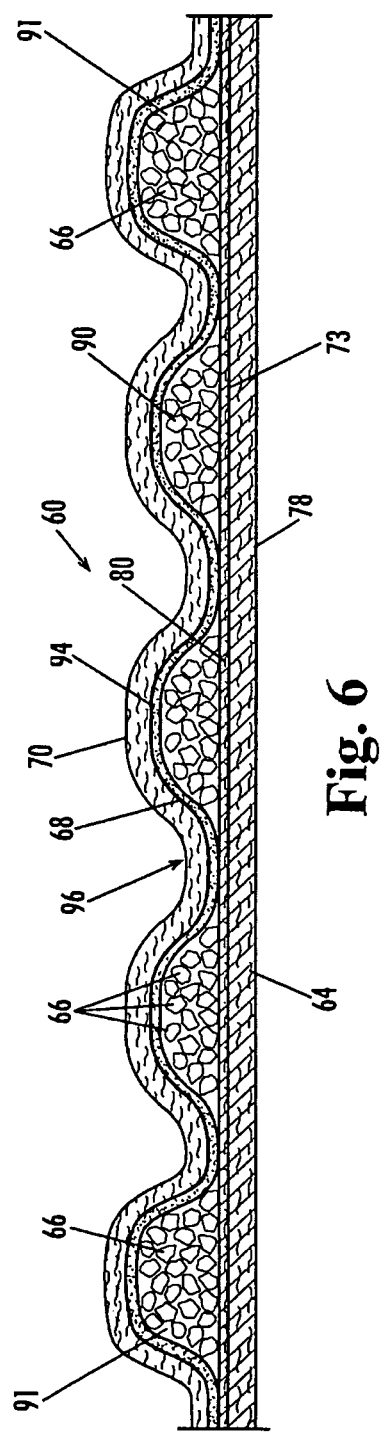
FIG. 6 is a partial cross sectional view of an example absorbent material core layer of a waistcap/waistband in accordance with an embodiment of this invention wherein more absorbent particulate polymer material is present toward lateral edges of the diaper than in a central zone of the diaper.
Figure 9:
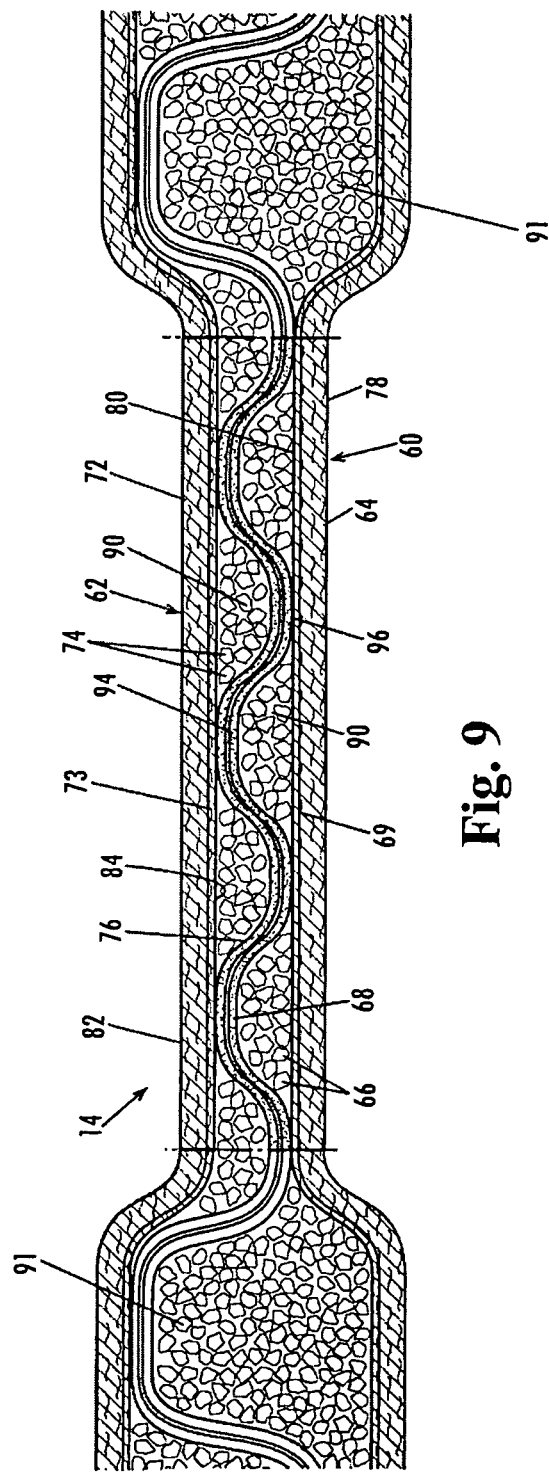
FIG. 9 is a cross-sectional view of an example absorbent material core of a waistcap/waistband comprising a combination of the first and second absorbent material layers illustrated in FIGS. 7 and 8.

As shown in FIGS. 5 and 9, a thermoplastic adhesive material 68 and 76 may serve to cover and at least partially immobilize the absorbent particulate polymer material 66 and 74. In one embodiment of the invention, the thermoplastic adhesive material 68 and 76 may be disposed essentially uniformly within the absorbent particulate polymer material 66 and 74, between the polymers. However, in a certain embodiment, the thermoplastic adhesive material 68 and 76 may be provided as a fibrous layer which is at least partially in contact with the absorbent particulate polymer material 66 and 74 and partially in contact with the substrate layers 64 and 72 of the first and second absorbent layers 60 and 62. In one embodiment, the absorbent particulate polymer material 66 and 74 may be provided as a discontinuous layer, and a layer of fibrous thermoplastic adhesive material 68 and 76 is laid down onto the layer of absorbent particulate polymer material 66 and 74, such that the thermoplastic adhesive material 68 and 76 is in direct contact with the absorbent particulate polymer material 66 and 74, but also in direct contact with the second surfaces 80 and 84 of the substrates 64 and 72, where the substrates are not covered by the absorbent particulate polymer material 66 and 74. This imparts an essentially three-dimensional structure to the fibrous layer of thermoplastic adhesive material 68 and 76, which in itself is essentially a two-dimensional structure of relatively small thickness, as compared to the dimension in length and width directions. In other words, the thermoplastic adhesive material 68 and 76 undulates between the absorbent particulate polymer material 68 and 76 and the second surfaces of the substrates 64 and 72.

Thereby, the thermoplastic adhesive material 68 and 76 may provide cavities to cover the absorbent particulate polymer material 66 and 74, and thereby immobilizes this material. In a further aspect, the thermoplastic adhesive material 68 and 76 bonds to the substrates 64 and 72 and thus affixes the absorbent particulate polymer material 66 and 74 to the substrates 64 and 72. Thus, in accordance with certain embodiments, the thermoplastic adhesive material 68 and 76 immobilizes the absorbent particulate polymer material 66 and 74 when wet, such that the absorbent material core 26 achieves an absorbent particulate polymer material loss of no more than about 70%, 60%, 50%, 40%, 30%, 20%, 10%, according to the Wet Immobilization Test described herein. Some thermoplastic adhesive materials will also penetrate into both the absorbent particulate polymer material 66 and 74 and the substrates 64 and 72, thus providing for further immobilization and affixation.

Of course, while the thermoplastic adhesive materials disclosed herein provide a much improved wet immobilization (i.e., immobilization of absorbent material when the article is wet or at least partially loaded), these thermoplastic adhesive materials may also provide a very good immobilization of absorbent material when the absorbent material core 26 is dry. The thermoplastic adhesive material 68 and 76 may also be referred to as a hot melt adhesive.

Without wishing to be bound by theory, it has been found that those thermoplastic adhesive materials which are most useful for immobilizing the absorbent particulate polymer material 66 and 74 combine good cohesion and good adhesion behavior. Good adhesion may promote good contact between the thermoplastic adhesive material 68 and 76 and the absorbent particulate polymer material 66 and 74 and the substrates 64 and 72. Good cohesion reduces the likelihood that the adhesive breaks, in particular in response to external forces, and namely in response to strain. When the absorbent material core 26 absorbs liquid, the absorbent particulate polymer material 66 and 74 swells and subjects the thermoplastic adhesive material 68 and 76 to external forces. In certain embodiments, the thermoplastic adhesive material 68 and 76 may allow for such swelling, without breaking and without imparting too many compressive forces, which would restrain the absorbent particulate polymer material 66 and 74 from swelling.

In accordance with certain embodiments, the thermoplastic adhesive material 68 and 76 may comprise, in its entirety, a single thermoplastic polymer or a blend of thermoplastic polymers, having a softening point, as determined by the ASTM Method D-36-95 "Ring and Ball", in the range between 50° C. and 300° C., or alternatively the thermoplastic adhesive material may be a hot melt adhesive comprising at least one thermoplastic polymer in combination with other thermoplastic diluents such as tackifying resins, plasticizers and additives such as antioxidants. In certain embodiments, the thermoplastic polymer has typically a molecular weight (Mw) of more than 10,000 and a glass transition temperature (Tg) usually below room temperature or $-6°$ C.$>T_g<16°$ C. In certain embodiments, typical concentrations of the polymer in a hot melt are in the range of about 20 to about 40% by weight. In certain embodiments, thermoplastic polymers may be water insensitive. Exemplary polymers are (styrenic) block copolymers including A-B-A triblock structures, A-B diblock structures and (A-B)n radial block copolymer structures wherein the A blocks are non-elastomeric polymer blocks, typically comprising polystyrene, and the B blocks are unsaturated conjugated diene or (partly) hydrogenated versions of such. The B block is typically isoprene, butadiene, ethylene/butylene (hydrogenated butadiene), ethylene/propylene (hydrogenated isoprene), and mixtures thereof.

Other suitable thermoplastic polymers that may be employed are metallocene polyolefins, which are ethylene polymers prepared using single-site or metallocene catalysts. Therein, at least one comonomer can be polymerized with ethylene to make a copolymer, terpolymer or higher order polymer. Also applicable are amorphous polyolefins or amorphous polyalphaolefins (APAO) which are homopolymers, copolymers or terpolymers of C2 to C8 alpha olefins.

In exemplary embodiments, the tackifying resin has typically a Mw below 5,000 and a Tg usually above room temperature, typical concentrations of the resin in a hot melt are in the range of about 30 to about 60%, and the plasticizer has a low Mw of typically less than 1,000 and a Tg below room temperature, with a typical concentration of about 0 to about 15%.

In certain embodiments, the thermoplastic adhesive material 68 and 76 is present in the form of fibers. In some embodiments, the fibers will have an average thickness of about 1 to about 50 micrometers or about 1 to about 35 micrometers and an average length of about 5 mm to about 50 mm or about 5 mm to about 30 mm. To improve the adhesion of the thermoplastic adhesive material 68 and 76 to the substrates 64 and 72 or to any other layer, in particular any other nonwoven layer, such layers may be pre-treated with an auxiliary adhesive.

In certain embodiments, the thermoplastic adhesive material 68 and 76 will meet at least one, or several, or all of the following parameters:

An exemplary thermoplastic adhesive material 68 and 76 may have a storage modulus G' measured at 20° C. of at least 30,000 Pa and less than 300,000 Pa, or less than 200,000 Pa, or between 140,000 Pa and 200,000 Pa, or less than 100,000 Pa. In a further aspect, the storage modulus G' measured at 35° C. may be greater than 80,000 Pa. In a further aspect, the storage modulus G' measured at 60° C. may be less than 300,000 Pa and more than 18,000 Pa, or more than 24,000 Pa, or more than 30,000 Pa, or more than 90,000 Pa. In a further aspect, the storage modulus G' measured at 90° C. may be less than 200,000 Pa and more than 10,000 Pa, or more than 20,000 Pa, or more than 30,000 Pa. The storage modulus measured at 60° C. and 90° C. may be a measure for the form stability of the thermoplastic adhesive material at elevated ambient temperatures. This value is particularly important if the absorbent product is used in a hot climate where the thermoplastic adhesive material would lose its integrity if the storage modulus G' at 60° C. and 90° C. is not sufficiently high. In a further embodiment, the thermoplastic adhesive material 68 and 76 may have a deformation resistance strain in % between about 20 and about 90.

The absorbent material core 26 may also comprise an auxiliary adhesive which is not illustrated in the figures. The auxiliary adhesive may be deposited on the first and second substrates 64 and 72 of the respective first and second absorbent layers 60 and 62 before application of the absorbent particulate polymer material 66 and 74 for enhancing adhesion of the absorbent particulate polymer materials 66 and 74 and the thermoplastic adhesive material 68 and 76 to the respective substrates 64 and 72. The auxiliary glue may also aid in immobilizing the absorbent particulate polymer material 66 and 74 and may comprise the same thermoplastic adhesive material as described hereinabove or may also comprise other adhesives including but not limited to sprayable hot melt adhesives, such as H.B. Fuller Co. (St. Paul, Minn.) Product No. HL-1620-B. The auxiliary glue may be applied to the substrates by any suitable means, but according to certain embodiments, may be applied in about 0.5 mm to about 1 mm wide slots spaced about 0.5 mm to about 2 mm apart.

The cover layer may comprise the same material as the substrates 64 and 72, or may comprise a different material. In certain embodiments, suitable materials for the cover layer are the nonwoven materials, typically the materials described above as useful for the substrates 64 and 72.

The diaper may further comprise an acquisition system (not shown) disposed between the upper waistcap/waistband layer 46 and a wearer facing side of the absorbent material core 26. The acquisition system may be in direct contact with the absorbent material core 26. The acquisition system may comprise a single layer or multiple layers, such as an upper acquisition layer facing towards the wearer's skin and a lower acquisition layer facing the garment of the wearer. According to a certain embodiment, the acquisition system may function to receive a surge of liquid, such as a gush of urine. In other words, the acquisition system may serve as a temporary reservoir for liquid until the absorbent material core 26 can absorb the liquid.

In a certain embodiment, the acquisition system may comprise chemically cross-linked cellulosic fibers. Such cross-linked cellulosic fibers may have desirable absorbency properties. Exemplary chemically cross-linked cellulosic fibers are disclosed in U.S. Pat. No. 5,137,537. In certain embodiments, the chemically cross-linked cellulosic fibers are cross-linked with between about 0.5 mole % and about 10.0 mole % of a $C_2$ to $C_9$ polycarboxylic cross-linking agent or between about 1.5 mole % and about 6.0 mole % of a $C_2$ to $C_9$ polycarboxylic cross-linking agent based on glucose unit. Citric acid is an exemplary cross-linking agent. In other embodiments, polyacrylic acids may be used. Further, according to certain embodiments, the cross-linked cellulosic fibers have a water retention value of about 25 to about 60, or about 28 to about 50, or about 30 to about 45. A method for determining water retention value is disclosed in U.S. Pat. No. 5,137,537. According to certain embodiments, the cross-linked cellulosic fibers may be crimped, twisted, or curled, or a combination thereof including crimped, twisted, and curled.

In a certain embodiment, one or both of the upper and lower acquisition layers may comprise a non-woven, which may be hydrophilic. Further, according to a certain embodiment, one or both of the upper and lower acquisition layers may comprise the chemically cross-linked cellulosic fibers, which may or may not form part of a nonwoven material. According to an exemplary embodiment, the upper acquisition layer may comprise a nonwoven, without the cross-linked cellulosic fibers, and the lower acquisition layer may comprise the chemically cross-linked cellulosic fibers. Further, according to an embodiment, the lower acquisition layer may comprise the chemically cross-linked cellulosic fibers mixed with other fibers such as natural or synthetic polymeric fibers. According to exemplary embodiments, such other natural or synthetic polymeric fibers may include high surface area fibers, thermoplastic binding fibers, polyethylene fibers, polypropylene fibers, PET fibers, rayon fibers, lyocell fibers, and mixtures thereof. According to a particular embodiment, the lower acquisition layer has a total dry weight, the cross-linked cellulosic fibers are present on a dry weight basis in the upper acquisition layer in an amount from about 30% to about 95% by weight of the lower acquisition layer, and the other natural or synthetic polymeric fibers are present on a dry weight basis in the lower acquisition layer in an amount from about 70% to about 5% by weight of the lower acquisition layer. According to another embodiment, the cross-linked cellulosic fibers are present on a dry weight basis in the first acquisition layer in an amount from about 80% to about 90% by weight of the lower acquisition layer, and the other natural or synthetic polymeric fibers are present on a dry weight basis in the lower acquisition layer in an amount from about 20% to about 10% by weight of the lower acquisition layer.

According to a certain embodiment, the lower acquisition layer desirably has a high fluid uptake capability. Fluid uptake is measured in grams of absorbed fluid per gram of absorbent material and is expressed by the value of "maximum uptake." A high fluid uptake corresponds therefore to a high capacity of the material and is beneficial, because it ensures the complete acquisition of fluids to be absorbed by an acquisition material. According to exemplary embodiments, the lower acquisition layer has a maximum uptake of about 10 g/g.

A relevant attribute of the upper acquisition layer is its Median Desorption Pressure, MDP. The MDP is a measure of the capillary pressure that is required to dewater the lower acquisition layer to about 50% of its capacity at 0 cm capillary suction height under an applied mechanical pressure of 0.3 psi. Generally, a relatively lower MDP may be useful. The lower MDP may allow the lower acquisition layer to more efficiently drain the upper acquisition material. Without wishing to be bound by theory, a given distribution material may have a definable capillary suction. The ability of the lower acquisition layer to move liquid vertically via capillary forces will be directly impacted by gravity and the opposing capillary forces associated with desorption of the upper acquisition layer. Minimizing these capillary forces may positively impact the performance of the lower acquisition layer. However, in a certain embodiment the lower acquisition layer may also have adequate capillary absorption suction in order to drain the layers above (upper acquisition layer and upper waistcap/waistband layer 46, in particular) and to temporarily hold liquid until the liquid can be partitioned away by the absorbent core components. Therefore, in a certain embodiment, the lower acquisition layer may have a minimum MDP of greater than 5 cm. Further, according to exemplary embodiments, the lower acquisition layer has an MDP value of less than about 20.5 cm $H_2O$, or less than about 19 cm $H_2O$, or less than about 18 cm $H_2O$ to provide for fast acquisition.

The methods for determining MDP and maximum uptake are disclosed in U.S. patent application Ser. No. 11/600,691 (Flohr et al.). For example, according to a first embodiment, the lower acquisition layer may comprise about 70% by weight of chemically cross-linked cellulose fibers, about 10% by weight polyester (PET), and about 20% by weight untreated pulp fibers. According to a second embodiment, the lower acquisition layer may comprise about 70% by weight chemically cross-linked cellulose fibers, about 20% by weight lyocell fibers, and about 10% by weight PET fibers. According to a third embodiment, the lower acquisition layer may comprise about 68% by weight chemically cross-linked cellulose fibers, about 16% by weight untreated pulp fibers, and about 16% by weight PET fibers. In one embodiment, the lower acquisition layer 54 may comprise from about 90% to about 100% by weight chemically cross-linked cellulose fibers.

Suitable non-woven materials for the upper and lower acquisition layers include, but are not limited to, SMS material, comprising a spunbonded, a melt-blown and a further spunbonded layer. In certain embodiments, permanently hydrophilic nonwovens, and in particular, nonwovens with durably hydrophilic coatings are desirable. Another suitable embodiment comprises a SMMS-structure. In certain embodiments, the nonwovens are porous.

In certain embodiments, suitable non-woven materials may include, but are not limited to synthetic fibers, such as PE, PET, and PP. As polymers used for nonwoven production may be inherently hydrophobic, they may be coated with hydrophilic coatings. One way to produce nonwovens with durably hydrophilic coatings, is via applying a hydrophilic monomer and a radical polymerization initiator onto the nonwoven, and conducting a polymerization activated via UV light resulting in monomer chemically bound to the surface of the nonwoven as described in co-pending U.S. Patent Publication No. 2005/0159720. Another way to produce nonwovens with durably hydrophilic coatings is to coat the nonwoven with hydrophilic nanoparticles as described in co-pending applications U.S. Pat. No. 7,112,621 to Rohrbaugh et al. and in PCT Application Publication WO 02/064877.

Typically, nanoparticles have a largest dimension of below 750 nm. Nanoparticles with sizes ranging from 2 to 750 nm may be economically produced. An advantage of nanoparticles is that many of them can be easily dispersed in water solution to enable coating application onto the nonwoven, they typically form transparent coatings, and the coatings applied from water solutions are typically sufficiently durable to exposure to water. Nanoparticles can be organic or inorganic, synthetic or natural. Inorganic nanoparticles generally exist as oxides, silicates, and/or carbonates. Typical examples of suitable nanoparticles are layered clay minerals (e.g., LAPONITE™ from Southern Clay Products, Inc. (USA), and Boehmite alumina (e.g., Disperal P2™ from North American Sasol. Inc.). According to a certain embodiment, a suitable nanoparticle coated non-woven is that disclosed in the co-pending patent application Ser. No. 10/758,066 entitled "Disposable absorbent article comprising a durable hydrophilic core wrap" to Ekaterina Anatolyevna Ponomarenko and Mattias NMN Schmidt.

Further useful nonwovens are described in U.S. Pat. No. 6,645,569 to Cramer et al., U.S. Pat. No. 6,863,933 to Cramer et al., U.S. Pat. No. 7,112,621 to Rohrbaugh et al., and co-pending U.S. patent application Ser. No. 10/338,603 to Cramer et al. and Ser. No. 10/338,610 to Cramer et al.

In some cases, the nonwoven surface can be pre-treated with high energy treatment (corona, plasma) prior to application of nanoparticle coatings. High energy pre-treatment typically temporarily increases the surface energy of a low surface energy surface (such as PP) and thus enables better wetting of a nonwoven by the nanoparticle dispersion in water.

Notably, permanently hydrophilic nonwovens are also useful in other parts of an absorbent article. For example, topsheets and absorbent material core layers comprising permanently hydrophilic nonwovens as described above have been found to work well.

According to a certain embodiment, the upper acquisition layer may comprise a material that provides good recovery when external pressure is applied and removed. Further, according to a certain embodiment, the upper acquisition layer may comprise a blend of different fibers selected, for example from the types of polymeric fibers described above. In some embodiments, at least a portion of the fibers may exhibit a spiral-crimp which has a helical shape. In some embodiments, the upper acquisition layer may comprise fibers having different degrees or types of crimping, or both. For example, one embodiment may include a mixture of fibers having about 8 to about 12 crimps per inch (cpi) or about 9 to about 10 cpi, and other fibers having about 4 to about 8 cpi or about 5 to about 7 cpi. Different types of crimps include, but are not limited to a 2D crimp or "flat crimp" and a 3D or spiral-crimp. According to a certain embodiment, the fibers may include bi-component fibers, which are individual fibers each comprising different materials, usually a first and a second polymeric material. It is believed that the use of side-by-side bi-component fibers is beneficial for imparting a spiral-crimp to the fibers.

The upper acquisition layer may be stabilized by a latex binder, for example a styrene-butadiene latex binder (SB latex), in a certain embodiment. Processes for obtaining such lattices are known, for example, from EP 149 880 (Kwok) and US 2003/0105190 (Diehl et al.). In certain embodiments, the binder may be present in the upper acquisition layer 52 in excess of about 12%, about 14% or about 16% by weight. For certain embodiments, SB latex is available under the trade name GENFLO™ 3160 (OMNOVA Solutions Inc.; Akron, Ohio).

The absorbent material core 26 shown in FIGS. 5-10 generally is disposed between an upper waistcap/waistband layer 46 and a lower waistcap/waistband layer 48, and comprises two intermediate layers, such as a first absorbent layer 60 and a second absorbent layer 62. As best shown in FIG. 5, the first absorbent layer 60 of the absorbent material core 26 comprises a substrate 64, an absorbent particular polymer material 66 on the substrate 64, and a thermoplastic composition 68 on the absorbent particulate polymer material 66 and at least portions of the first substrate 64 as an adhesive for covering and immobilizing the absorbent particulate polymer material 66 on the first substrate 64. According to another embodiment illustrated in FIG. 7, the first absorbent layer 60 of the absorbent material core 26 may also include a cover layer 70 on a thermoplastic composition 68. The absorbent material core 26 may also include another layer 69 of thermoplastic composition on the first substrate 64 for anchoring the absorbent particulate polymer material 66 to the first substrate 64.

Likewise, as best illustrated in FIG. 9, the second absorbent layer 62 of the absorbent material core 26 may also include a substrate 72, a thermoplastic composition 73 on the substrate, an absorbent particulate polymer material 74 adhered to the second substrate 72 with the thermoplastic composition, and a thermoplastic composition 66 on the absorbent particulate polymer material 74 and at least a portion of the second substrate 72 or first layer of thermoplastic composition for immobilizing the absorbent particulate polymer material 74 on the second substrate 72. Although not illustrated, the second absorbent layer 62 may also include a cover layer such as the cover layer 70 illustrated in FIG. 6.

The substrate 64 of the first absorbent layer 60 may be referred to as a dusting layer and has a first surface 78 which faces the lower waistcap/waistband layer 48 of the waistcap/waistband 20, 22, and a second surface 80 which faces the absorbent particulate polymer material 66. Likewise, the substrate 72 of the second absorbent layer 62 may be referred to as a core cover and has a first surface 82 facing the upper waistcap/waistband layer 46 of the waistcap/waistband 20, 22, and a second surface 84 facing the absorbent particulate polymer material 74. The first and second substrates 64 and 72 may be adhered to one another with adhesive about the periphery to form an envelope about the absorbent particulate polymer materials 66 and 74 to hold the absorbent particulate polymer material 66 and 74 within the absorbent material core 26.

According to a certain embodiment, the substrates 64 and 72 of the first and second absorbent layers 60 and 62 may be a non-woven material, such as those nonwoven materials described above. In certain embodiments, the non-wovens are porous and in one embodiment has a pore size of about 32 microns.

As illustrated in FIGS. 5-10, the absorbent particulate polymer material 66 and 74 is deposited on the respective substrates 64 and 72 of the first and second absorbent layers 60 and 62 in small and large clusters 90 and 91 of particles to form a grid pattern 92 comprising land areas 94 and junction areas 96 between the land areas 94. As defined herein, land areas 94 are areas where the thermoplastic adhesive material does not contact the nonwoven substrate or the auxiliary adhesive directly; junction areas 96 are areas where the thermoplastic adhesive material does contact the nonwoven substrate or the auxiliary adhesive directly. The junction areas 96 in the grid pattern 92 contain little or no absorbent particulate polymer material 66 and 74. The land areas 94 and junction areas 96 can have a variety of shapes including, but not limited to, circular, oval, square, rectangular, triangular, and the like.

The small clusters 90 of absorbent particulate polymer material 66 and 74 are relatively thinner than the large clusters 91 of absorbent particulate polymer material 66 and 74 and impart a lower basis weight of absorbent particulate polymer material 66 and 74 to the area of the absorbent material core 26 in which the small clusters 90 are located. Likewise, the large clusters 91 of absorbent particulate polymer material 66 and 74 are relatively thicker than the small clusters 90 of absorbent particulate polymer material 66 and 74 and impart a higher basis weight of absorbent particulate polymer material 66 and 74 to the area of the absorbent material 26 in which the large clusters 91 are located. This creates a varied profile of absorbent particulate polymer material across the absorbent material core 26.

Figure 10:
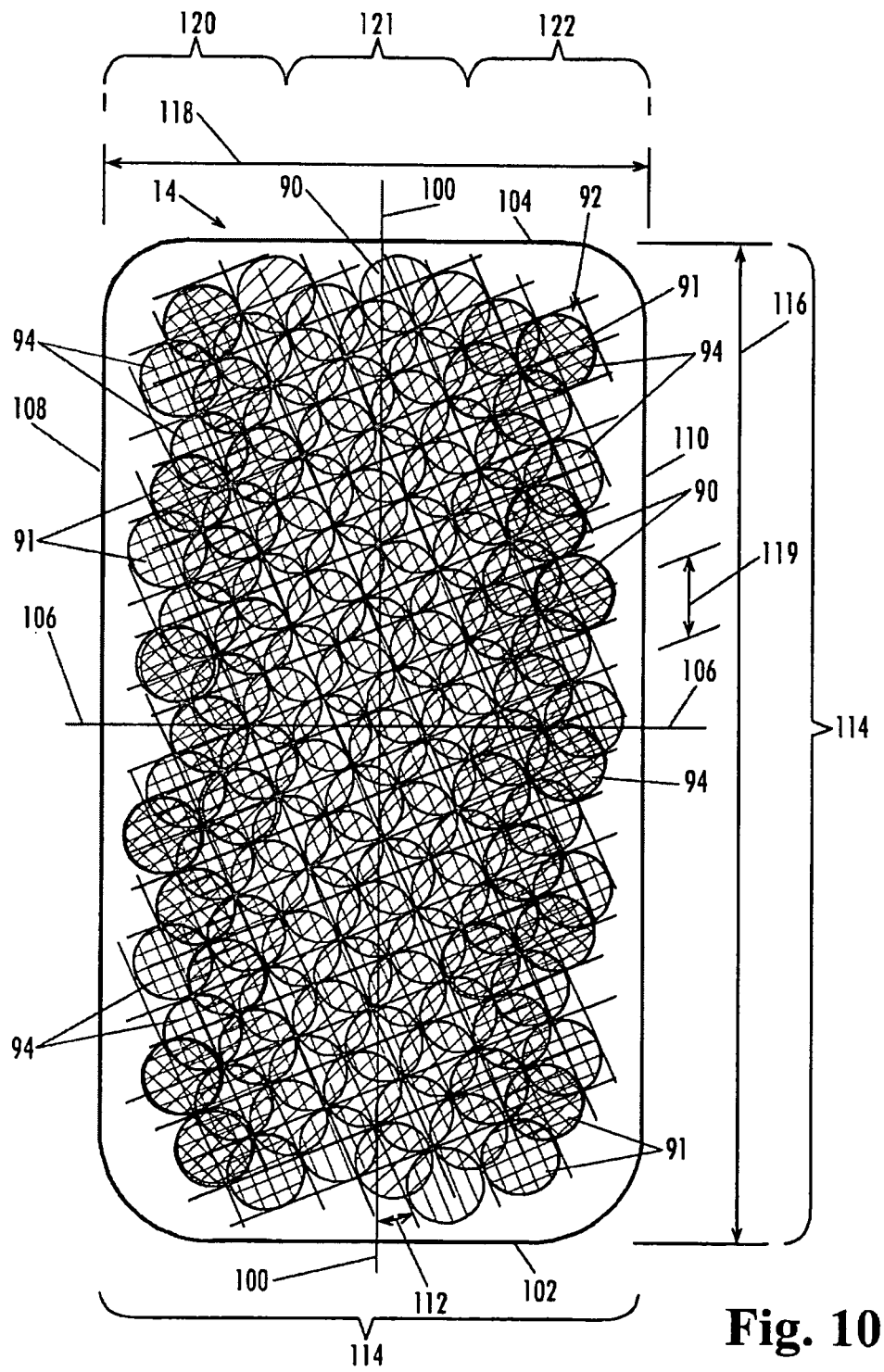
FIG. 10 is a plan view of the example absorbent material core illustrated in FIG. 9.

The grid pattern shown in FIG. 10 is a square grid with regular spacing and size of the land areas. Other grid patterns including hexagonal, rhombic, orthorhombic, parallelogram, triangular, rectangular, and combinations thereof may also be used. The spacing between the grid lines may be regular or irregular.

The size of the land areas 94 in the grid patterns 92 may vary. According to certain embodiments, the width 119 of the land areas 94 in the grid patterns 92 ranges from about 8 mm to about 12 mm. In a certain embodiment, the width of the land areas 94 is about 10 mm. The junction areas 96, on the other hand, in certain embodiments, have a width or larger span of less than about 5 mm, less than about 3 mm, less than about 2 mm, less than about 1.5 mm, less than about 1 mm, or less than about 0.5 mm.

As shown in FIG. 10, the absorbent material core 26 has a longitudinal axis 100 extending from a rear end 102 to a front end 104 and a transverse axis 106 perpendicular to the longitudinal axis 100 extending from a first edge 108 to a second edge 110. The grid pattern 92 of absorbent particulate polymer material clusters 90 and 91 is arranged on the substrates 64 and 72 of the respective absorbent layers 60 and 62 such that the grid pattern 92 formed by the arrangement of land areas 94 and junction areas 96 forms a pattern angle 112. The pattern angle 112 may be greater than 0, or 15 to 30 degrees, or from about 5 to about 85 degrees, or from about 10 to about 60 degrees, or from about 15 to about 30 degrees.

As best seen in FIGS. 9 and 10, the first and second layers 60 and 62 may be combined to form the absorbent material core 26. The absorbent material core 26 has an absorbent particulate polymer material area 114 bounded by a pattern length 116 and a pattern width 118. The extent and shape of the absorbent particulate polymer material area 114 may vary depending on the desired application of the absorbent material core 26 and the particular absorbent article in which it may be incorporated. In a certain embodiment, however, the absorbent particulate polymer material area 114 extends substantially entirely across the absorbent material core 26, such as is illustrated in FIG. 10.

The first and second absorbent layers 60 and 62 may be combined together to form the absorbent material core 26 such that the grid patterns 92 of the respective first and second absorbent layers 62 and 64 are offset from one another along the length and/or width of the absorbent material core 26. The respective grid patterns 92 may be offset such that the absorbent particulate polymer material 66 and 74 is substantially continuously distributed across the absorbent particulate polymer area 114. In a certain embodiment, absorbent particulate polymer material 66 and 74 is substantially continuously distributed across the absorbent particulate polymer material area 114 despite the individual grid patterns 92 comprising absorbent particulate polymer material 66 and 74 discontinuously distributed across the first and second substrates 64 and 72 in clusters 90 and 91. In a certain embodiment, the grid patterns may be offset such that the land areas 94 of the first absorbent layer 60 face the junction areas 96 of the second absorbent layer 62 and the land areas of the second absorbent layer 62 face the junction areas 96 of the first absorbent layer 60. When the land areas 94 and junction areas 96 are appropriately sized and arranged, the resulting combination of absorbent particulate polymer material 66 and 74 is a substantially continuous layer of absorbent particular polymer material across the absorbent particulate polymer material area 114 of the absorbent material core 26 (i.e. first and second substrates 64 and 72 do not form a plurality of pockets, each containing a cluster 90 of absorbent particulate polymer material 66 therebetween). In a certain embodiment, respective grid patterns 92 of the first and second absorbent layer 60 and 62 may be substantially the same.

In certain embodiments as illustrated in FIGS. 5-10, the amount of absorbent particulate polymer material 66 and 74 may vary along the width 116 of the grid pattern 92 substantially perpendicularly to the longitudinal axis 36 of disposable absorbent diaper 10. In a certain embodiment, the grid pattern may be divided into absorbent zones 120, 121 and 122, in which the amount of absorbent particulate polymer material 66 and 74 per unit area of the absorbent material core 26 varies from zone to zone. As used herein, "absorbent zone" refers to a region of the absorbent particulate polymer material area having boundaries that are perpendicular to the longitudinal axis shown in FIG. 10. The amount of absorbent particulate polymer material 66 and 74 may, in a certain embodiment, gradually transition from one of the plurality of absorbent zones 120, 121, and 122 to another. This gradual transition in amount of absorbent particulate polymer material 66 and 74 may reduce the possibility of cracks forming in the absorbent material core 26.

The amount of absorbent particulate polymer material 66 and 74 present in the absorbent material core 26 may vary, but in certain embodiments, is present in the material core in an amount greater than about 80% by weight of the absorbent material core, or greater than about 85% by weight of the absorbent material core, or greater than about 90% by weight of the absorbent material core, or greater than about 95% by weight of the absorbent material core. In a particular embodiment, the absorbent material core 26 consists essentially of the first and second substrates 64 and 72, the absorbent particulate polymer material 66 and 74, and the thermoplastic adhesive composition 68 and 76. In an embodiment, the absorbent material core 26 may be substantially cellulose free.

According to certain embodiments, the weight of absorbent particulate polymer material 66 and 74 in at least one freely selected first square measuring 1 cm×1 cm may be at least about 10%, or 20%, or 30%, 40% or 50% higher than the weight of absorbent particulate polymer material 66 and 74 in at least one freely selected second square measuring 1 cm×1 cm. In a certain embodiment, the first and the second square are centered about the longitudinal axis.

Method and Apparatus for Making Absorbent Materials for Waistcaps/Waistbands

A printing system 130 for making an absorbent material core 26 for a waistcap/waistband 20, 22 in accordance with an embodiment of this invention is illustrated in FIG. 12 and may generally comprise a first printing unit 132 for forming the first absorbent layer 60 of the absorbent material core 26 and a second printing unit 134 for forming the second absorbent layer 62 of the absorbent material core 26.

The first printing unit 132 may comprise a first auxiliary adhesive applicator 136 for applying an auxiliary adhesive 69 to the substrate 64, which may be a nonwoven web, a first rotatable support roll 140 for receiving the substrate 64, a hopper 142 for holding absorbent particulate polymer material 66, a printing roll 144 for transferring the absorbent particulate polymer material 66 to the substrate 64, and a thermoplastic adhesive material applicator 146 for applying the thermoplastic adhesive material 68 to the substrate 64 and the absorbent particulate polymer 66 material thereon.

The second printing unit 134 may comprise a second auxiliary adhesive applicator 148 for applying an auxiliary adhesive 73 to the second substrate 72, a second rotatable support roll 152 for receiving the second substrate 72, a second hopper 154 for holding the absorbent particulate polymer material 74, a second printing roll 156 for transferring the absorbent particulate polymer material 74 from the hopper 154 to the second substrate 72, and a second thermoplastic adhesive material applicator 158 for applying the thermoplastic adhesive material 76 to the second substrate 72 and the absorbent particulate polymer material 74 thereon.

The printing system 130 also includes a guide roller 160 for guiding the formed absorbent material core from a nip 162 between the first and second rotatable support rolls 140 and 152.

The first and second auxiliary applicators 136 and 148 and the first and second thermoplastic adhesive material applicators 146 and 158 may be a nozzle system which can provide a relatively thin but wide curtain of thermoplastic adhesive material.

Figure 13:
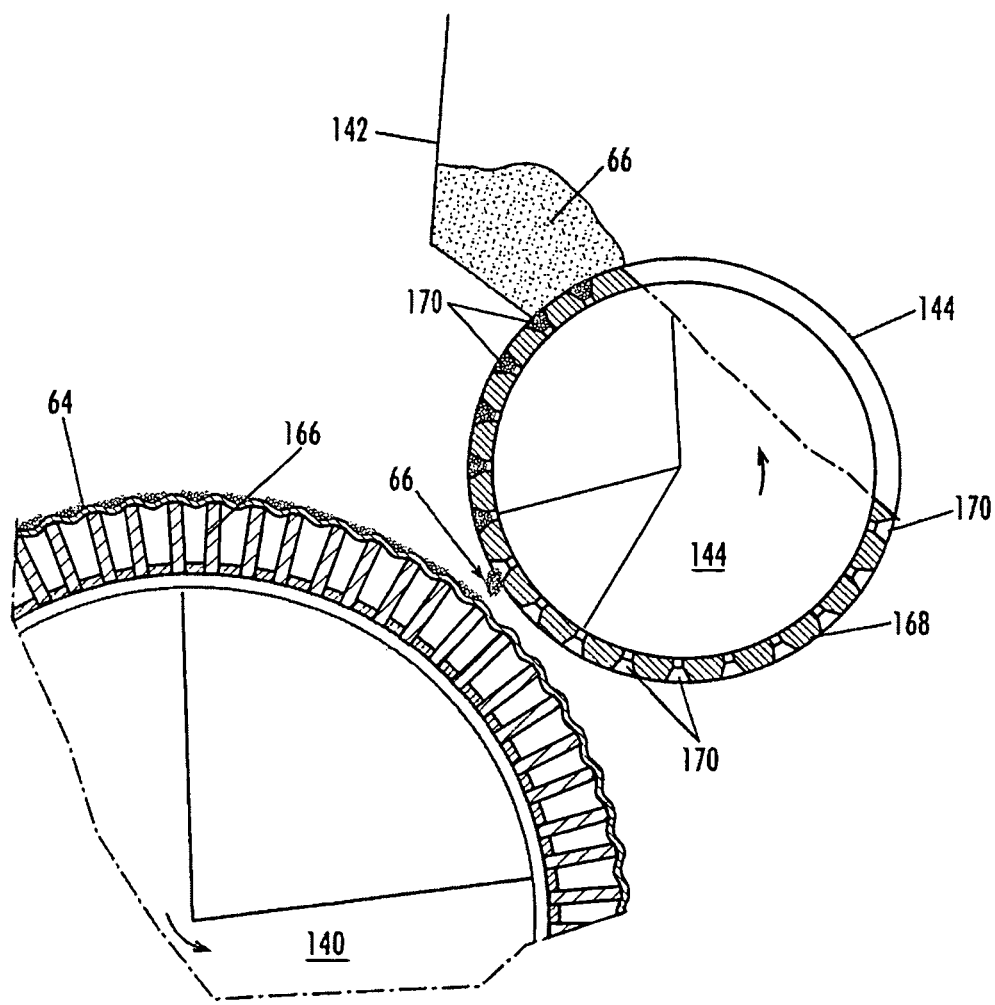
FIG. 13 is a partial sectional view of an apparatus for making an example absorbent material core of a waistcap/waistband in accordance with an embodiment of the invention.
Figure 16:
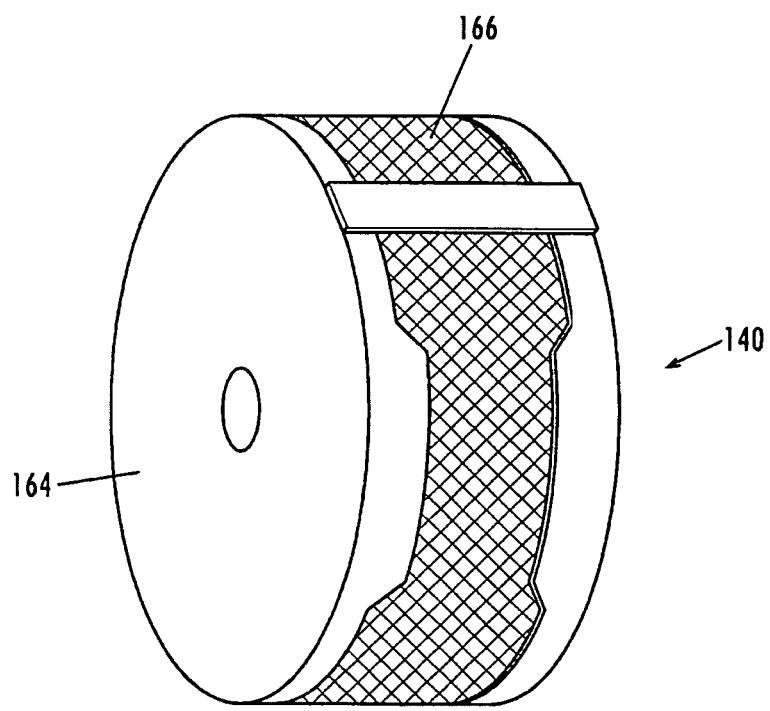
FIG. 16 is a perspective view of the supporting roll illustrated in FIG. 14.

Turning to FIG. 13, portions of the first hopper 142, first support roll 140, and first printing roll 144 are illustrated. As also shown in FIG. 16, the first rotatable support roll 140, which has the same structure as the second rotatable support roll 152, comprises a rotatable drum 164 and a peripheral vented support grid 166 for receiving the first substrate 64.

Figure 14:
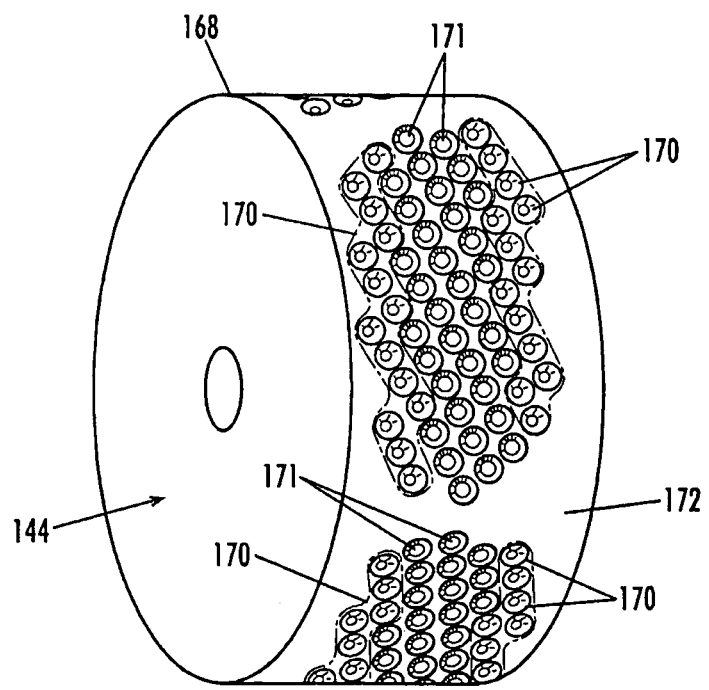
FIG. 14 is a perspective view of the printing roll illustrated in FIG. 13.

As also illustrated in FIG. 14, the first printing roll 144, which has the same structure as the second printing roll 156, comprises a rotatable drum 168 and a plurality of absorbent particulate polymer material reservoirs 170 and 171 in a peripheral surface 172 of the drum 168. The reservoirs 170 and 171, best illustrated in FIG. 15, may have a variety of shapes, including cylindrical, conical, or any other shape. The reservoirs 170 and 171 may lead to an air passage 174 in the drum 168 and comprise a vented cover 176 for holding adhesive particulate polymer material 66 in the reservoir and preventing the adhesive particulate polymer material 66 from falling or being pulled into the air passage 174.

Figure 7:
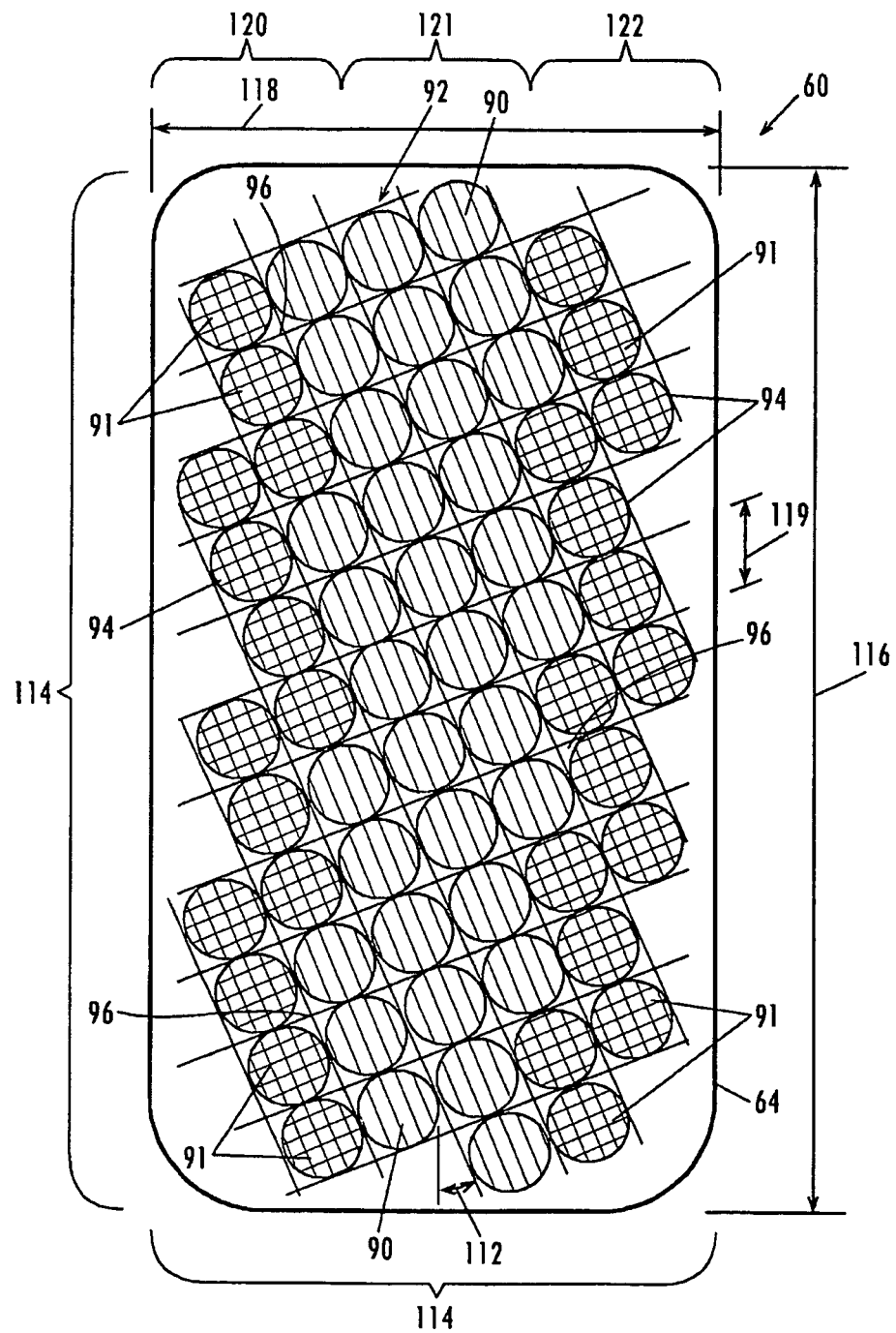
FIG. 7 is a plan view of the example absorbent core layer illustrated in FIG. 6.
Figure 15:
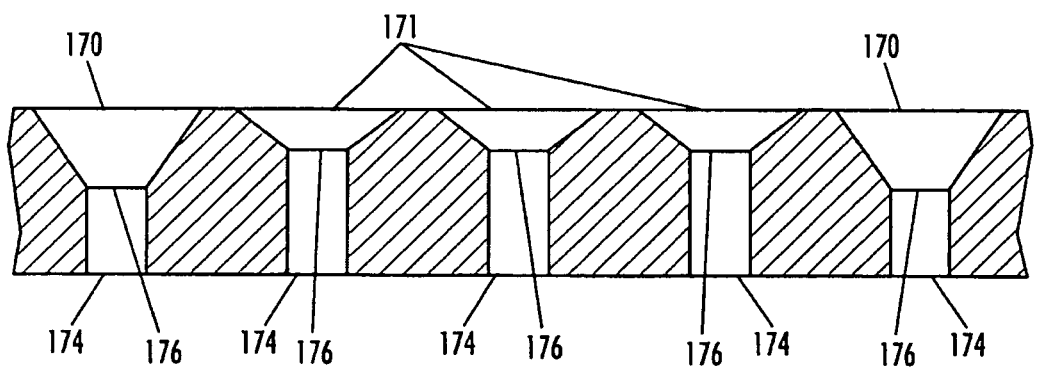
FIG. 15 is a partial sectional view of the printing roll illustrated in FIG. 14 showing absorbent particulate polymer material reservoirs.

The first printing roll 144 is designed to produce a certain embodiment like the absorbent material core 26 illustrated in FIG. 7 wherein side absorbent zones 120 and 122 have a higher basis weight of absorbing particulate polymer material 66 and 74 than the central absorbent zone 121. In the embodiment illustrated in FIG. 14, this effect may be achieved by having a corresponding set of reservoirs 170 which are relatively deep and a second set 171 of reservoirs which are relatively shallow, such that the deeper reservoirs 170 carry more absorbent particulate polymer material and deliver more absorbent particulate polymer material 66 to the side absorbent zones 120 and 122 and the more shallow reservoirs 171 hold less adhesive particulate polymer material and deliver less absorbent particulate polymer material 66 to the central zone 121 of the absorbent material core 26. The sets of deeper and shallower reservoirs 170 and 171, of course, can be arranged in any variety of patterns or configurations to create an absorbent material core 26 with any corresponding variety of varying absorbent particulate polymer material basis weights across the absorbent material core 26. FIG. 15, in particular, illustrates the difference in volumetric sizes of first and second sets of reservoirs 170 and 171.

Other methods of delivering a varying profile of absorbent particulate polymer basis weights to the absorbent material core 26 include, but are not limited to, applying a higher vacuum in sections of the first and second rotatable support rolls 140 and 152 where more absorbent particulate polymer material is desired or, when the absorbent particulate polymer material is delivered to the absorbent core substrate 64 pneumatically, such as when combining cellulosic fibers with absorbent particulate polymer material, directing the air stream carrying the absorbent particulate polymer material and cellulosic fibers to areas of the absorbent core substrate where a higher basis weight of absorbent particulate polymer material is desired.

Figure 8:
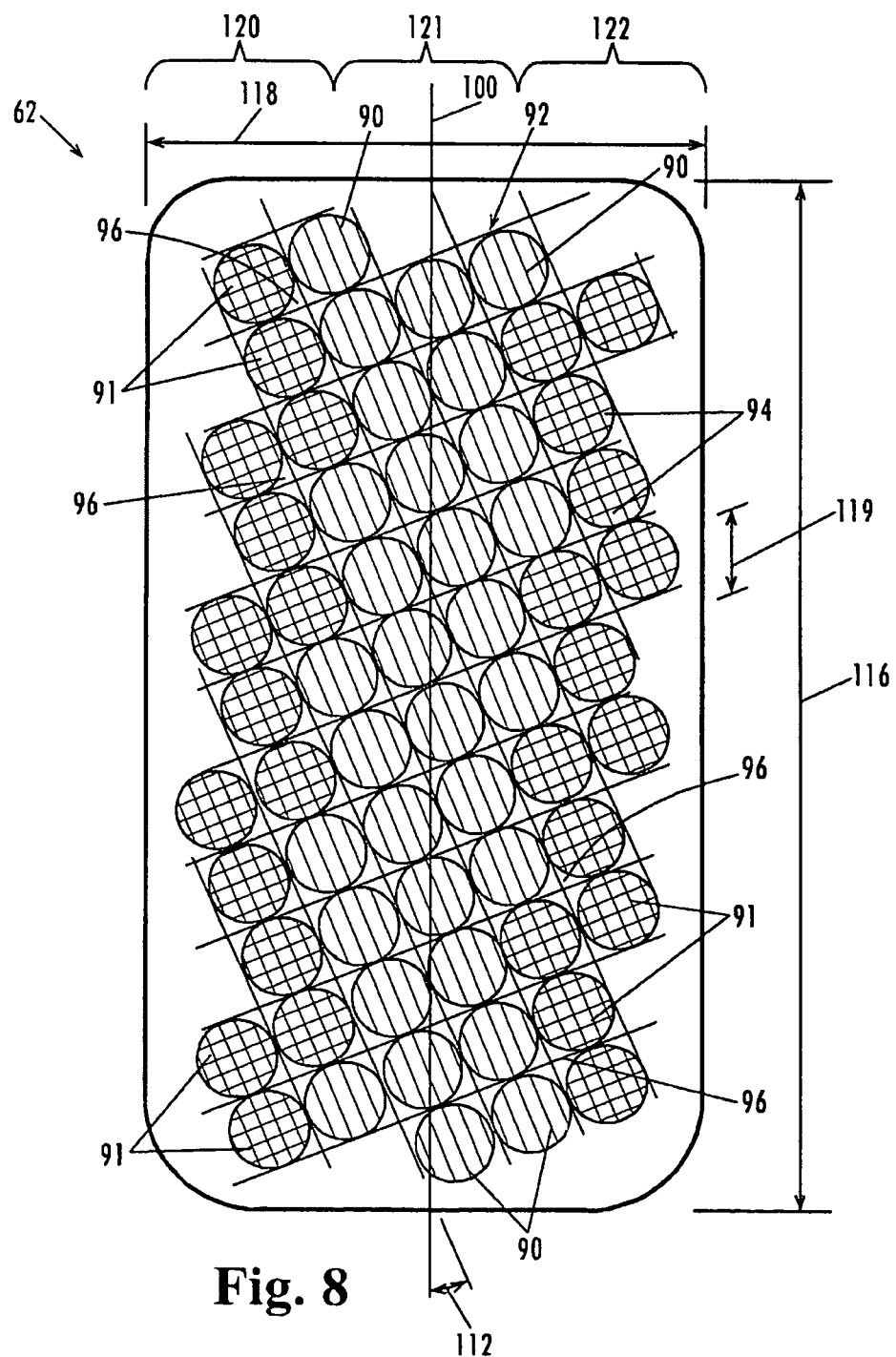
FIG. 8 is a plan view of a second absorbent core layer of a waistcap/waistband in accordance with an embodiment of the invention wherein more absorbent particulate polymer material is present toward lateral edges of the waistcap/waistband than in a central zone of the waistcap/waistband.

In operation, the printing system 130 receives the first and second substrate 64 and 72 into the first and second printing units 132 and 134, respectively, the first substrate 64 is drawn by the rotating first support roll 140 past the first auxiliary adhesive applicator 136 which applies the first auxiliary adhesive to the first substrate 64 in a pattern such as described hereinabove. A vacuum (not shown) within the first support roll 140 draws the first substrate 64 against the vertical support grid 166 and holds the first substrate 64 against the first support roll 140. This presents an uneven surface on the first substrate 64. Due to gravity, or by using the vacuum means, the substrate 64 will follow the contours of the uneven surface and thereby the substrate 64 will assume a mountain and valley shape. The absorbent particulate polymer material 66 may accumulate in the valleys presented by the substrate 64. The first support roll 140 then carries the first substrate 64 past the rotating first printing roll 144 which transfers the absorbent particulate polymer material 66 from the first hopper 142 to the first substrate 64 in the grid pattern 92 which is best illustrated in FIGS. 7 and 8. A vacuum (not shown) in the first printing roll 144 may hold the absorbent particulate polymer material 66 in the reservoirs 170 until time to deliver the absorbent particulate polymer material 66 to the first substrate 64. The vacuum may then be released or air flow through the air passages 174 may be reversed to eject the absorbent particulate polymer material 66 from the reservoirs and onto the first substrate 64. The absorbent particulate polymer material 66 may accumulate in the valleys presented by the substrate 64. The support roll 140 then carries the printed first substrate 64 past the thermoplastic adhesive material applicator 136 which applies the thermoplastic adhesive material 68 to cover the absorbent particulate polymer material 66 on the first substrate 64.

Hence, the uneven surface of the vented support grid 166 of the support rolls 140 and 152 determines the distribution of absorbent particulate polymeric material 66 and 74 throughout the absorbent material core 26 and likewise determines the pattern of junction areas 96.

Meanwhile, the second rotatable support roll draws the second substrate 72 past the second auxiliary adhesive applicator 148 which applies an auxiliary adhesive to the second substrate 72 in a pattern such as is described hereinabove. The second rotatable support roll 152 then carries the second substrate 72 past the second printing roll 156 which transfers the absorbent particulate polymer material 74 from the second hopper 154 to the second substrate 72 and deposits the absorbent particulate polymer material 74 in the grid pattern 92 on the second substrate 72 in the same manner as described with regard to the first printing unit 132 above. The second thermoplastic adhesive material applicator 158 then applies the thermoplastic adhesive material 76 to cover the absorbent particulate polymer material 74 on the second substrate 72. The printed first and second substrates 64 and 72 then pass through the nip 162 between the first and second support rolls 140 and 152 for compressing the first absorbent layer 60 and second absorbent layer 62 together to form the absorbent material core 26.

In an optional further process step a cover layer 70 may be placed upon the substrates 64 and 72, the absorbent particulate polymer material 66 and 74, and the thermoplastic adhesive material 68 and 76. In another embodiment, the cover layer 70 and the respective substrate 64 and 72 may be provided from a unitary sheet of material. The placing of the cover layer 70 onto the respective substrate 64 and 72 may then involve the folding of the unitary piece of material.

Figure 17:
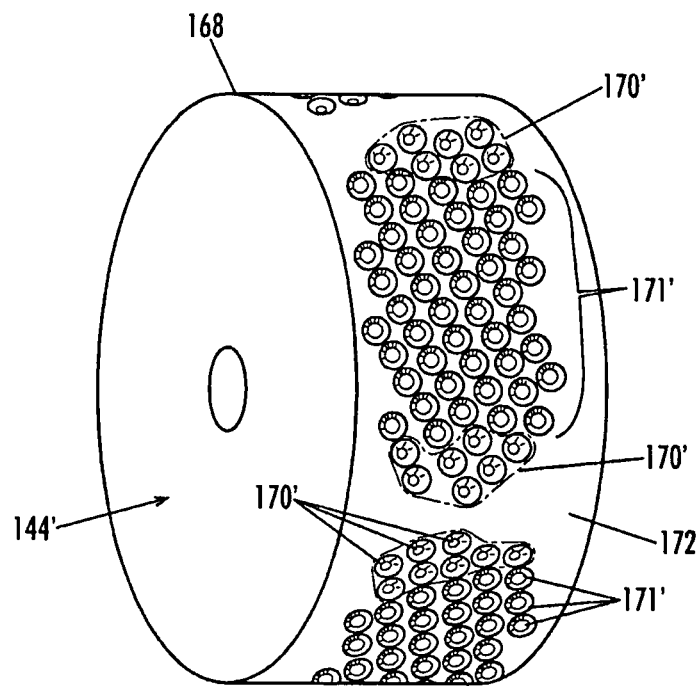
FIG. 17 is a perspective view of a printing roll for making an embodiment of the invention wherein more absorbent particulate polymer material is present toward ends of the waistcap/waistband than in a central zone of the waistcap/waistband.
Figure 18:
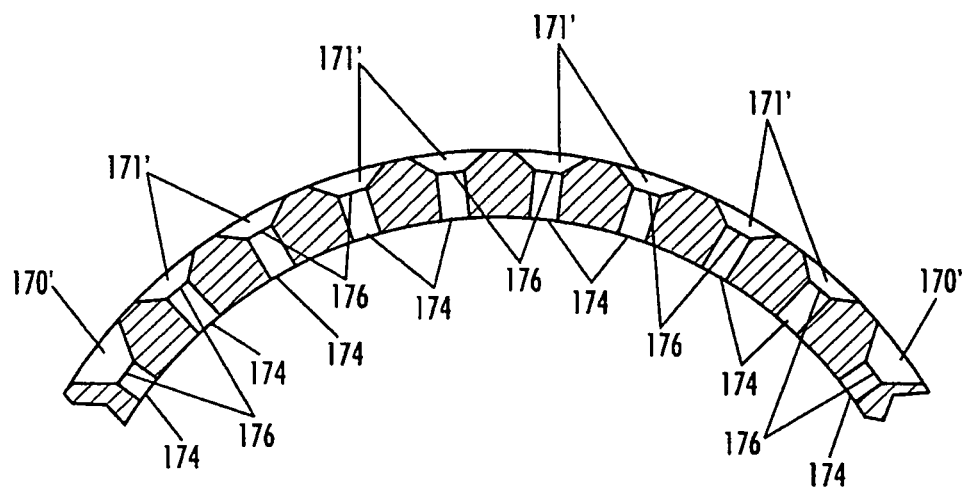
FIG. 18 is a partial sectional view of the printing roll illustrated in FIG. 17 showing absorbent particulate polymer material reservoirs.
Figure 19:
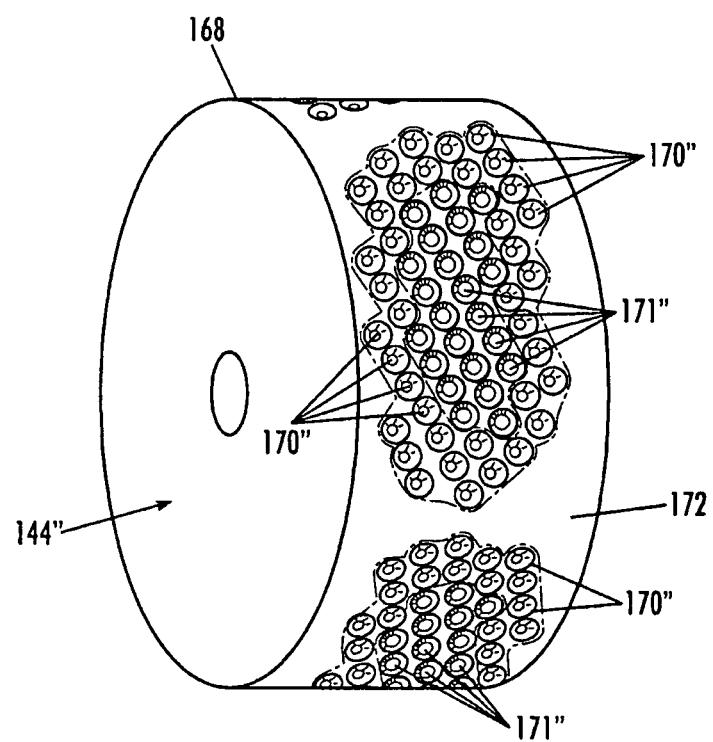
FIG. 19 is a perspective view of a printing roll for making an embodiment of the invention wherein more absorbent particulate polymer material is present toward lateral edges and ends of the waistcap/waistband than in a central zone of the waistcap/waistband.
Figure 20:
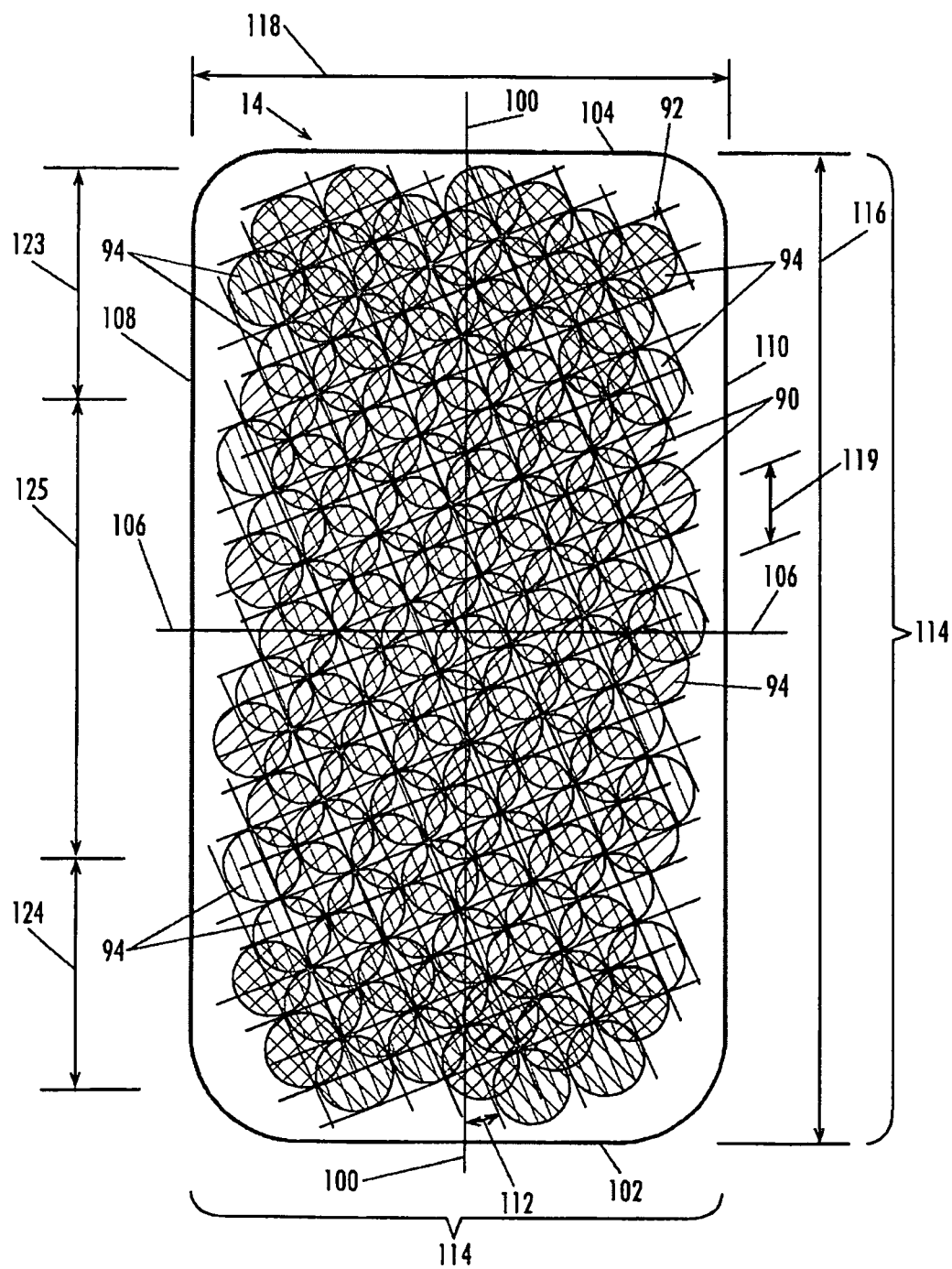
FIG. 20 is a plan view of an example absorbent material core of a waistcap/waistband in accordance with an embodiment of the invention wherein more absorbent particulate polymer material is present toward ends of the waistcap/waistband than in a central zone of the waistcap/waistband.
Figure 21:
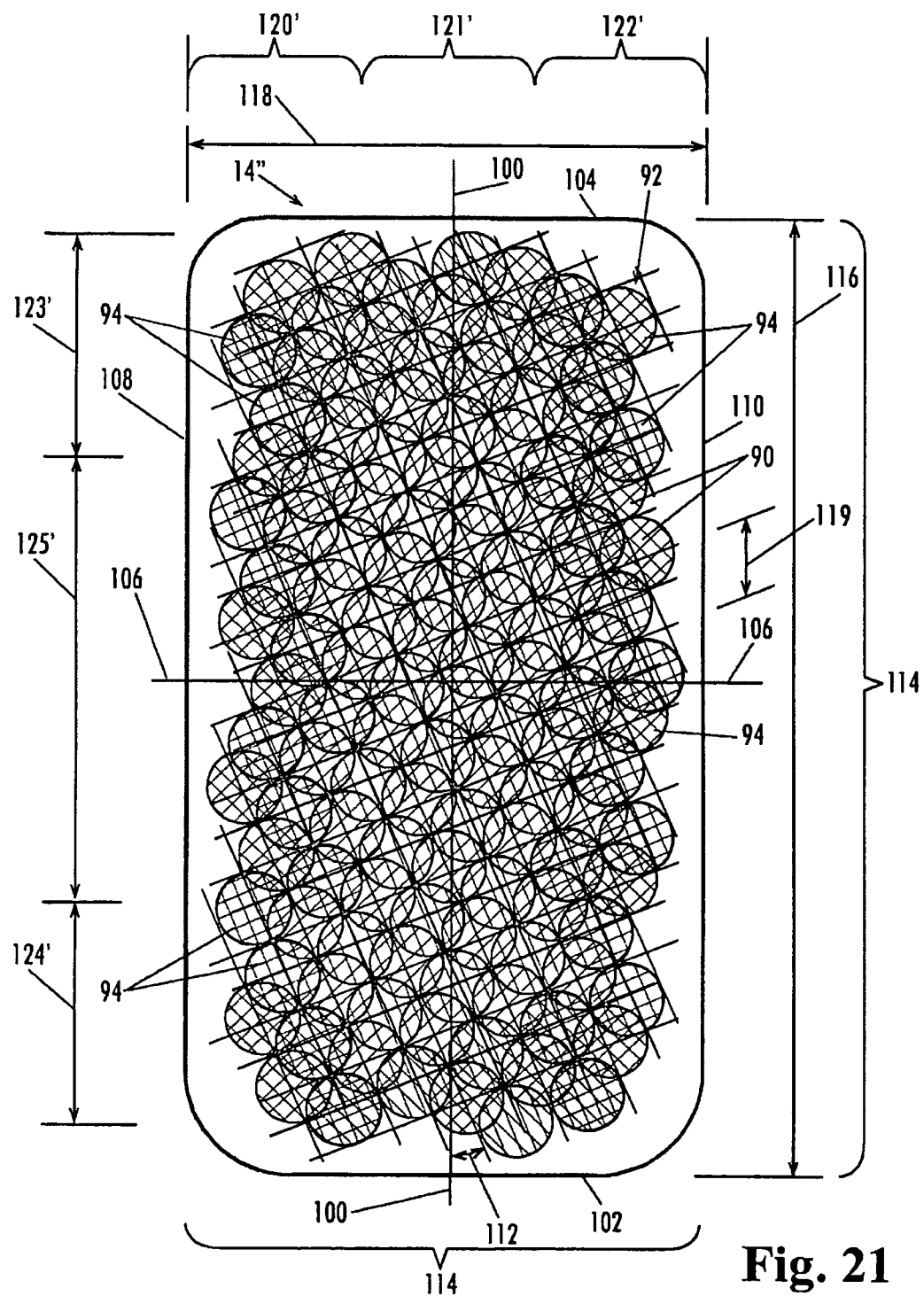
FIG. 21 is a plan view of another example absorbent material core of a waistcap/waistband in accordance with an embodiment of the invention wherein more absorbent particulate polymer material is present toward lateral edges and ends of the waistcap/waistband than in a central zone of the waistcap/waistband.
Figure 22:
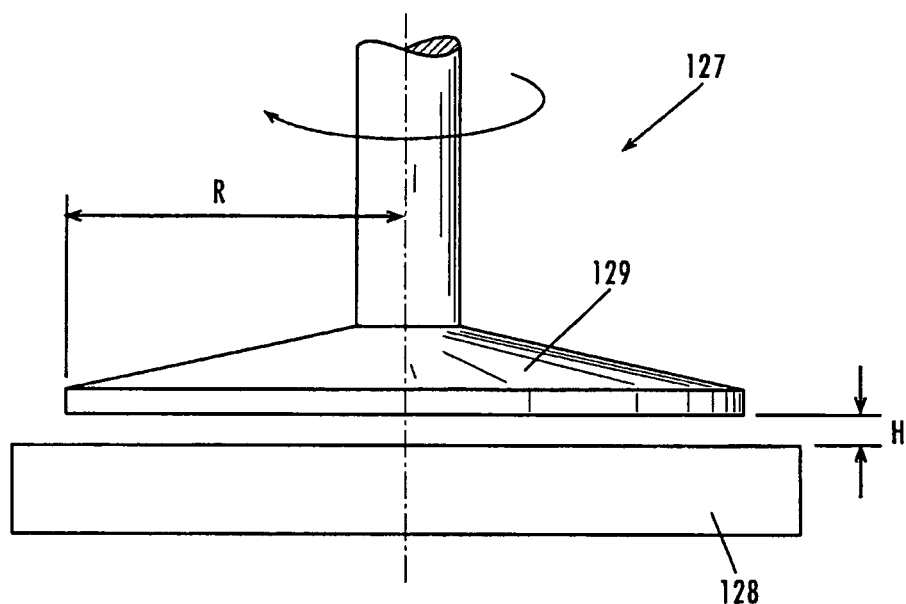
FIG. 22 is a schematic representation of a rheometer.

FIGS. 17-19 illustrate certain embodiments of printing rolls 144' and 144" for making corresponding embodiments of absorbent material cores 26' and 26" illustrated in FIGS. 20 and 21, respectively. As shown in FIGS. 17 and 18, the printing roll 144' for making the absorbent material core 26' illustrated in FIG. 20 comprises sets of deeper and shallower reservoirs 170' and 171' for forming the end absorbent zones 123 and 124, which have a higher absorbent particulate polymer material basis weight, and the central absorbent zone 125, which has a lower absorbent particulate polymer material basis weight, respectively. Likewise, the printing roll 144" in FIG. 19 for making the absorbent material core 26" in FIG. 21 has sets of deeper and shallower reservoirs 170" and 171", respectively, for forming the side absorbent zones 120' and 122' and end absorbent zones 123' and 124', having a higher basis weight of absorbent particulate polymer material, and the central zone 121' and 125' having a lower basis weight of absorbent particulate polymer material.

Absorbent articles such as the diapers 10 made in accordance with embodiments of this invention may be folded and packaged for distribution and sale. Absorbent articles are typically bi-folded, but may also be tri-folded. After folding, the folded absorbent articles may be stacked to form a stack comprising a plurality of absorbent articles. The stack may then be compressed and encased in a packaging material such as a bag, a pouch, a box, or the like.

The test method and apparatuses described below may be useful in testing embodiments of this invention:

Wet Immobilization Test

Equipment
  Graduated Cylinder
  Stop watch (±0.1 sec)
  Scissors
  Light Box
  Pen
  Test solution: 0.90% saline solution at 37° C.
  Metal ruler traceable to NIST, DIN, JIS or other comparable National Standard
  PVC/metal dishes with a flat surface inside and a minimum length of the core bag length (n) to be measured and a maximum length n+30 mm, width of 105±5 mm, height of 30-80 mm or equivalent
  Electronic Force Gauge (Range 0 to 50 Kg)
  Wet Immobilization Impact Tester Equipment (WAIIT), Design package number: BM-00112.59500-R01 available from T.M.G. Technisches Buero Manfred Gruna Facilities:
  Standard laboratory conditions, temperature: 23° C.±2° C., relative humidity: <55%

Sample Preparation
  1. Open the product, topsheet side up.
  2. Unfold the diaper and cut the cuff elastics approximately every 2.5 cm to avoid chassis tension.
  3. For pull-up products open the side seams and remove the waistbands.
  4. Lay the core bag flat and rectangular topsheet side up onto the light box surface without any folds.
  5. Switch on the light box to clearly identify the absorbent core outer edges.
  6. With a ruler, draw a line at the front and back absorbent core outer edges.
  7. Measure the distance (A), between the two markers and divide the value by 2, this will be calculated distance (B).
  8. Measure the calculated distance (B) from front marker towards the middle of the core bag and mark it. At this marker draw a line in the cross direction.

Test Procedure

WAIIT Calibration:
  1. Make sure that the sliding board is in the lower position. Open the front door of the WAIIT tester and connect the force gauge hook to the upper sample clamp of the WAIIT. Make sure that the clamp is closed before connecting the spring-balance.
  2. Use both hands on the spring-balance to lift continuously and as slowly as possible up the sliding board towards the upper position. Record the average value ($m_1$) during the execution to the nearest 0.02 kg.
  3. Guide down the sliding board as slowly as possible to the lower position and record the average value ($m_2$) read off during execution to the nearest 0.02 kg.
  4. Calculate and report the delta of $m_1$-$m_2$ to the nearest 0.01 kg. If the delta is 0.6 kg±0.3 kg continue measurement. Otherwise, an adjustment of the sliding board is necessary. Make sure that the sliding board is in lower position and check the sliding path for any contamination or damage. Check if the position of the sliding board to the sliding path is correctly adjusted by shaking the board. For easy gliding some clearance is needed. If not present, readjust the system.

WAIIT Test Settings:
  Drop height is 50 cm.
  Diaper load ($I_D$) is 73% of the core capacity (cc); $I_D$=0.73×cc.
  Core capacity (cc) is calculated as: cc=$m_{SAP}$×$SAP_{GV}$, where $m_{SAP}$ is the mass of superabsorbent polymer (SAP) present in the diaper and $SAP_{GV}$ is the free swelling capacity of the superabsorbent polymer. Free swelling capacity of the superabsorbent polymer is determined with the method described in WO 2006/062258. The mass of the superabsorbent polymer present in the diaper is the average mass present in ten products.

Test Execution:
  1. Reset the balance to zero (tare), put the dry core bag on the balance, weigh and report it to the nearest 0.1 g.
  2. Measure the appropriate volume Saline (0.9% NaCl in deionized water) with the graduated cylinder.
  3. Lay the core bag, topsheet side up, flat into the PVC dish. Pour the saline evenly over the core bag.
  4. Take the PVC dish and hold it slanting in different directions, to allow any free liquid to be absorbed. Products with poly-backsheet need to be turned after a minimum waiting time of 2 minutes so that liquid under the backsheet can be absorbed. Wait for 10 minutes (±1 minute) to allow all saline to be absorbed. Some drops may retain in the PVC dish. Use only the defined PVC/metal dish to guarantee homogenous liquid distribution and less retained liquid.
  5. Reset the balance to zero (tare), put the wet core bag on the balance. Weigh and report it to the nearest 0.1 g. Fold the core bag just once to make it fit on the balance. Check to see if the wet core bag weight is out of limit (defined as "dry core bag weight+diaper load±4 ml"). For example, 12 g dry core bag weight+150 ml load=162 g wet core bag weight. If the actual wet weight on the scale is between 158 g and 166 g, the pad can be used for shaking. Otherwise scrap the pad and use the next one.
  6. Take the loaded core bag and cut the pad along the marked line in the cross direction.
  7. Put the back of the wet core bag onto the balance ($m_1$). Weigh and report it to the nearest 0.1 g.
  8. Take the wet core and clamp the end seal side in the top clamp of the sample holder of the WAIIT (open end of the core oriented down). Next, clamp both sides of the core with the side clamps of the sample holder making sure that the product is fixed to the sample holder along the whole product length. Make sure not to clamp the absorbent core, only the nonwoven; for some products this means securing the product with only the barrier leg cuff.
  9. Lift up the sliding board to the upper position by using both hands until the board is engaged.
  10. Close the safety front door and release the slide blade.
  11. Reset the balance to zero (tare), take the tested core bag out of the WAIIT and put it on the balance ($m_2$). Report the weight to the nearest 0.1 g.
  12. Repeat steps 7 to 11 with front of the wet core bag.

Reporting:
  1. Record the dry core bag weight to the nearest 0.1 g.
  2. Record the wet weight before ($m_{1\,front/back}$) and after ($m_{2\,front/back}$) testing, both to the nearest 0.1 g.
  3. Calculate and report the average weight loss ($\Delta m$) to the nearest 0.1 g: $\Delta m = (m_{1front} + m_{1back}) - (m_{2front} + m_{2back})$
  4. Calculate and report the weight loss in percent to the nearest 1%, ($\Delta m_{rel}$): $\Delta m_{rel} = (((m_{1front} + m_{1back}) - (m_{2front} + m_{2back})) \times 100)/(m_{1front} + m_{1back})$
  5. Calculate and report Wet Immobilization (WI) as: WI=100%−$\Delta m_{rel}$ All patents and patent applications (including any patents which issue thereon) assigned to the Procter & Gamble Company referred to herein are hereby incorporated by reference to the extent that it is consistent herewith.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

All documents cited in the Detailed Description of the Invention are, in relevant part, incorporated herein by reference; the citation of any document is not to be construed as an admission that it is prior art with respect to the present invention. To the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A disposable absorbent article comprising:
    an absorbent core having a garment surface and an opposed body surface, wherein the surfaces meet along at least one longitudinal edge and at least one end edge; wherein the at least one end edge is associated with multiple projections of the absorbent core;
    a liquid permeable topsheet positioned adjacent the body surface of the absorbent core and having a pair of opposed longitudinal edges;
    a liquid impermeable backsheet positioned adjacent the garment surface of the absorbent core; and
    a waistcap and/or waistband disposed adjacent to the multiple projections of the absorbent core,
    wherein the waistcap and/or waistband comprises an absorbent core material and is capable of absorbing moisture and subsequently deforming to fill at least a portion of space between the article and a portion of the wearer's body,
    wherein when one or more of the multiple projections are wetted by fluid and subsequently swell, the wetted projections elevate portions of the waistcap and/or waistband to form one or more channels between the waistcap and/or waistband and the projections so that fluid flows within the channels and away from the wearer's body.

2. The disposable absorbent article of claim 1, wherein at least a portion of the waistcap and/or waistband is positioned adjacent to a front edge of the article.

3. The disposable absorbent article of claim 1, wherein at least a portion of the waistcap and/or waistband is positioned adjacent to a back edge of the article.

4. The disposable absorbent article of claim 1, wherein the waistcap and/or waistband comprises a front waistcap and/or waistband portion positioned adjacent to a front edge of the article, and further comprises a back waistcap and/or waistband portion positioned adjacent to an opposing back edge of the article.

5. The disposable absorbent article of claim 1, wherein the waistcap and/or waistband is operable to be oriented adjacent to a wearer's waist.

6. The disposable absorbent article of claim 1, wherein at least a portion of the waistcap and/or waistband is operable to mount to both a left side cuff and a right side cuff.

7. The disposable absorbent article of claim 1, wherein the absorbent core comprises an absorbent particulate polymer material and which is substantially cellulose free.

8. The disposable absorbent article of claim 1, further comprising a nonwoven backsheet disposed between the absorbent core and the liquid impermeable backsheet.

9. The disposable absorbent article of claim 1, further comprising a pair of side panels.

10. The disposable absorbent article of claim 9, wherein the absorbent article is a diaper and the pair of side panels comprise a re-closable fastening system for securing the diaper to a wearer.

11. The disposable absorbent article of claim 9, comprising a pair of side panels that are joined to each other to form a pant.

12. A disposable absorbent article comprising:
    an absorbent core having a garment surface and an opposed body surface, wherein the surfaces meet along at least one longitudinal edge and at least one end edge, wherein the absorbent core comprises an absorbent particulate polymer material and which is substantially cellulose free; wherein the at least one end edge is associated with multiple projections of the absorbent core;
    a liquid permeable topsheet positioned adjacent the body surface of the absorbent core and having a pair of opposed longitudinal edges and a pair of opposed end edges;
    a liquid impermeable backsheet positioned adjacent the garment surface of the absorbent core; and
    a waistcap and/or waistband disposed adjacent to the multiple projections of the absorbent core,
    wherein when one or more of the multiple projections are wetted and subsequently deform, the wetted projections elevate portions of the waistcap and/or waistband to form one or more channels between the waistcap and/or waistband and the multiple projections so that fluid flows within the channels and away from the wearer's body, and
    wherein the waistcap and/or waistband comprises an absorbent core material and is operable to form a continuous gasket around the portion of the wearer's body.

* * * * *